United States Patent
Cowperthwait

(10) Patent No.: US 10,540,911 B2
(45) Date of Patent: Jan. 21, 2020

(54) MEDICAL TREATMENT SIMULATION DEVICES

(71) Applicant: Amy Cowperthwait, Newark, DE (US)

(72) Inventor: Amy Cowperthwait, Newark, DE (US)

(73) Assignee: University of Delaware, Newark, DE (US)

( * ) Notice: Subject to any disclaimer, the term of this patent is extended or adjusted under 35 U.S.C. 154(b) by 272 days.

(21) Appl. No.: 15/527,173

(22) PCT Filed: Nov. 16, 2015

(86) PCT No.: PCT/US2015/060889
§ 371 (c)(1),
(2) Date: May 16, 2017

(87) PCT Pub. No.: WO2016/081370
PCT Pub. Date: May 26, 2016

(65) Prior Publication Data
US 2017/0372639 A1  Dec. 28, 2017

Related U.S. Application Data

(60) Provisional application No. 62/145,018, filed on Apr. 9, 2015, provisional application No. 62/128,100, filed
(Continued)

(51) Int. Cl.
*G09B 23/28* (2006.01)
*G09B 23/30* (2006.01)

(52) U.S. Cl.
CPC ......... *G09B 23/285* (2013.01); *G09B 23/288* (2013.01); *G09B 23/303* (2013.01)

(58) Field of Classification Search
CPC ... G09B 23/285; G09B 23/288; G09B 23/303
(Continued)

(56) References Cited

U.S. PATENT DOCUMENTS

| 6,319,011 B1 | 11/2001 | Motti et al. |
| 8,342,852 B2 | 1/2013 | King |

(Continued)

FOREIGN PATENT DOCUMENTS

| CN | 2096789 U | 2/1992 |
| CN | 201004285 Y | 1/2008 |

(Continued)

OTHER PUBLICATIONS

Communication Pursuant to Article 94(3) for European Application No. 15 861 965.0, dated Apr. 8, 2019, 7 pages.
(Continued)

*Primary Examiner* — Robert P Bullington
(74) *Attorney, Agent, or Firm* — RatnerPrestia

(57) ABSTRACT

Medical treatment simulation systems and devices are disclosed. One device includes an overlay, a simulated treatment structure, at least one feedback device, and at least one processor. The overlay is configured to be secured to the live subject and to cover at least a portion of a body of the live subject. The simulated treatment structure is configured to simulate a structure associated with the medical procedure. The at least one feedback device is configured to provide a feedback signal to the live subject. The at least one processor is connected to the simulated treatment structure and the at least one feedback device. The processor is programmed to operate the feedback device to provide the feedback signal based upon input generated from interaction between a treatment provider and the simulated treatment structure. The disclosed devices may be used to simulate intravenous, catheter, defibrillation, and/or thoracic treatments.

5 Claims, 15 Drawing Sheets

Related U.S. Application Data on Mar. 4, 2015, provisional application No. 62/081,042, filed on Nov. 18, 2014, provisional application No. 62/080,444, filed on Nov. 17, 2014, provisional application No. 62/080,440, filed on Nov. 17, 2014, provisional application No. 62/080,439, filed on Nov. 17, 2014.

(58) Field of Classification Search
USPC .......................................................... 434/265
See application file for complete search history.

(56) References Cited

U.S. PATENT DOCUMENTS

| | | |
|---|---|---|
| 8,408,920 B2 | 4/2013 | Speller |
| 8,491,309 B2 | 7/2013 | Parry et al. |
| 8,882,511 B2 | 11/2014 | McKenzie et al. |
| 2007/0218438 A1 | 9/2007 | Sanders et al. |
| 2008/0171311 A1 | 7/2008 | Centen et al. |
| 2010/0062407 A1 | 3/2010 | Lecat |
| 2010/0185127 A1 | 7/2010 | Nilsson et al. |
| 2011/0223573 A1 | 9/2011 | Miller et al. |
| 2012/0091212 A1 | 4/2012 | Guilhamat et al. |
| 2012/0270197 A1 | 10/2012 | Brost et al. |
| 2012/0330200 A1 | 12/2012 | Voss et al. |
| 2013/0059279 A1 | 3/2013 | Reid-Searl et al. |
| 2013/0196302 A1 | 8/2013 | Lecat |
| 2013/0337425 A1 | 12/2013 | Allen et al. |
| 2014/0004494 A1 | 1/2014 | Greisser et al. |
| 2014/0302473 A1 | 10/2014 | Nakaguchi et al. |
| 2015/0024363 A1 | 1/2015 | Segall |
| 2015/0086958 A1 | 3/2015 | Lewis |

FOREIGN PATENT DOCUMENTS

| | | |
|---|---|---|
| CN | 201845491 U | 5/2011 |
| CN | 201886681 U | 6/2011 |
| CN | 202373225 U | 8/2012 |
| CN | 202523292 U | 11/2012 |
| CN | 202549149 U | 11/2012 |
| JP | 2005227534 A | 8/2005 |
| WO | 2009097045 A1 | 8/2009 |
| WO | 2009149090 A2 | 12/2009 |
| WO | 2011051172 A1 | 5/2011 |
| WO | 2012003023 A1 | 1/2012 |
| WO | 2013029081 A1 | 3/2013 |
| WO | 2015027286 A1 | 3/2015 |

OTHER PUBLICATIONS

Notice of Allowance for U.S. Appl. No. 15/661,529, dated Mar. 27, 2019, 16 pages.
Chinese Office Action for Chinese Application No. 201580069082.8, dated Dec. 24, 2018 with translation, 22 pages.
Non Final Office Action for U.S. Appl. No. 15/661,529, dated Jul. 20, 2018, 20 pages.
International Preliminary Report on Patentability and Written Opinion for International Application No. PCT/us2015/060889, dated May 23, 2017—8 Pages.
Advanced Patient Care Simulator S230.10. Male and Female Catheterization User Guide, Gaumard Scientific Company, 2012, pp. 1-16.
Castillo, C., "'Cut Suits' Help Soldiers Stay a Cut Above in Realistic Training Exercise", Joint Base San Antonio, Jun. 4, 2014, pp. 1-2, ,http://www.jbsa.af.mil/news/story.asp?id=123413317>.
Maternova, "Low-Cost Birth Simulator Kit", 2015, http://maternova.net.low-cost-birth-simulator-kit>.
Entire Patent Prosecution History of U.S. Appl. No. 14/466,027, filed Aug. 22, 2014, entitled, "Medical Treatment Simulation Devices".
Final Office Action for U.S. Appl. No. 14/496,396, dated Jul. 6, 2017, 15 pages.
International Search Report and Written Opinion for International Application No. PCT/US2015/060889, dated Apr. 14, 2016, 9 pages.
Entire Patent Prosecjution History of U.S. Appl. No. 14/496,396, filed Sep. 25, 2014, entitled "Medical Treatment Simulation Devices."
Non Final Office Action for U.S. Appl. No. 15/661,529, dated Aug. 23, 2017, 21 pages.
Extended European Search Report for European Application No. 15 861 965.0, dated Jun. 14, 2018, 8 pages.
Final Office Action for U.S. Appl. No. 15/661,529, dated Dec. 7, 2017, 30 pages.
Chinese Office Action for Chinese Application No. 201580069082.8 dated Sep. 12, 2019, with translation, 21 pages.

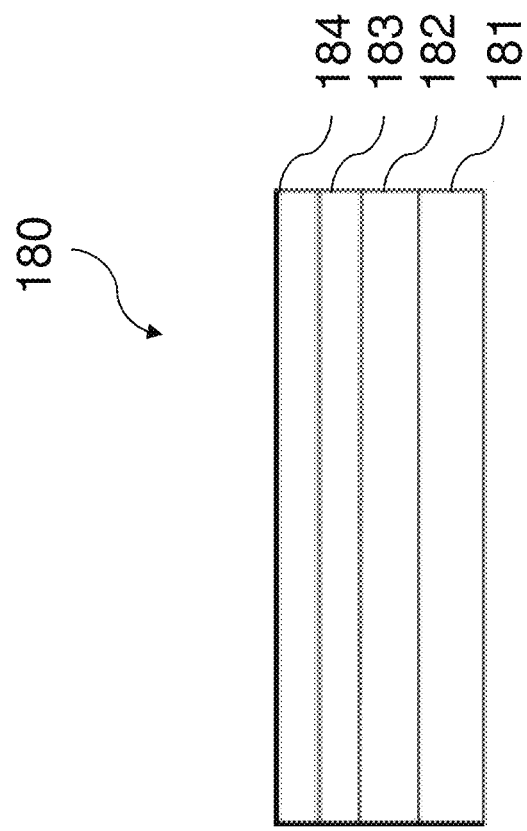
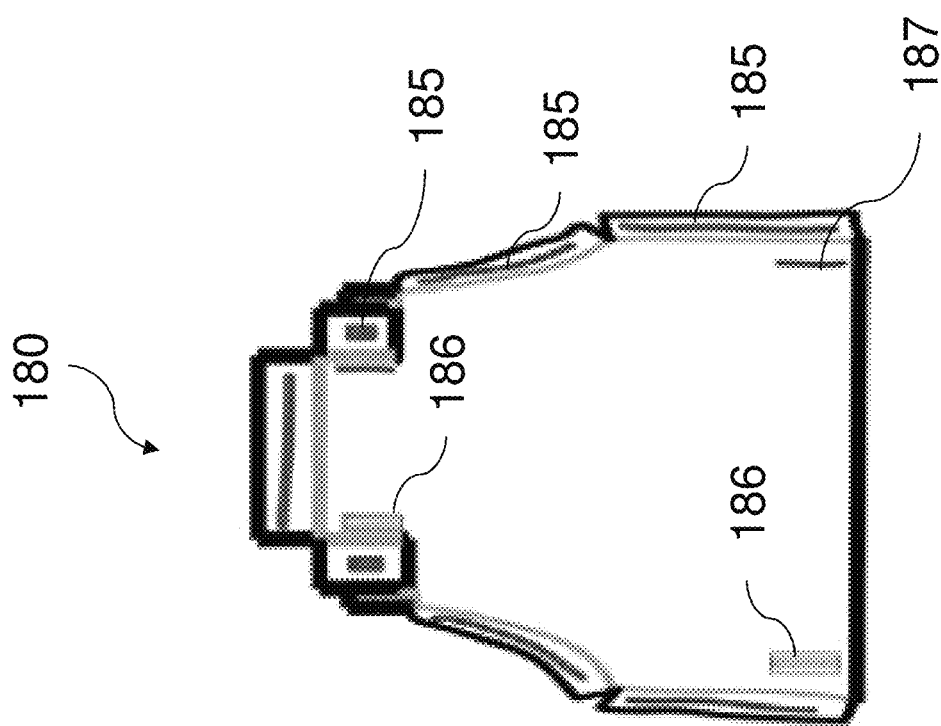
FIG. 6B
FIG. 6A

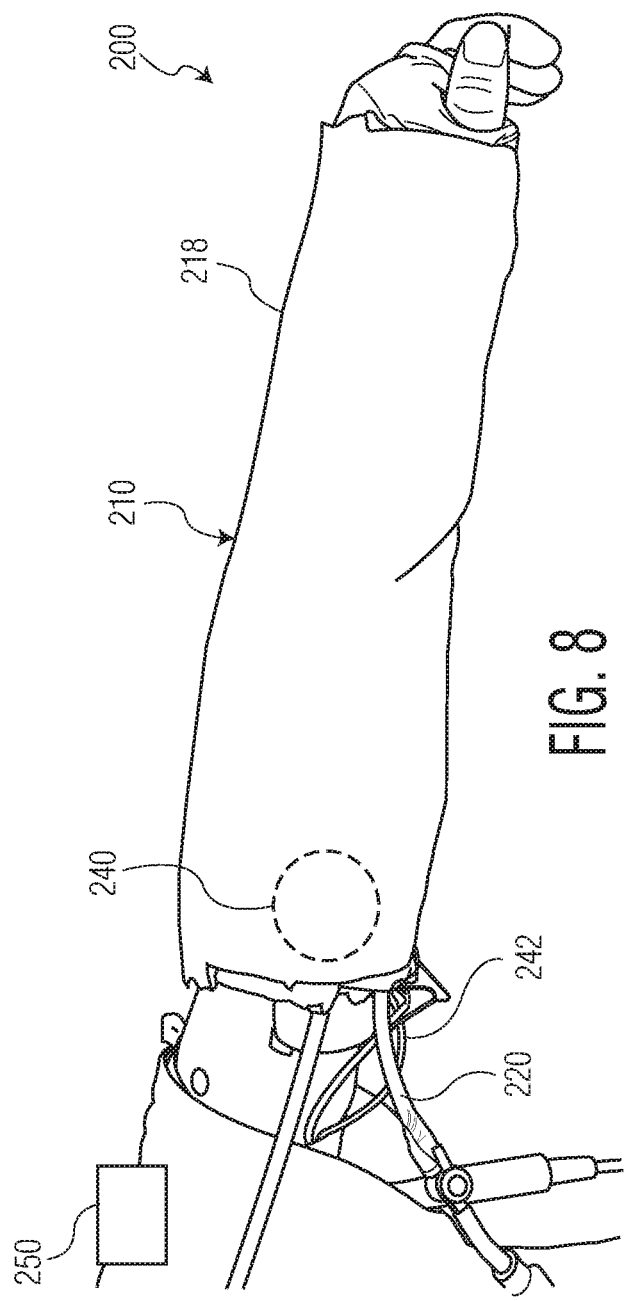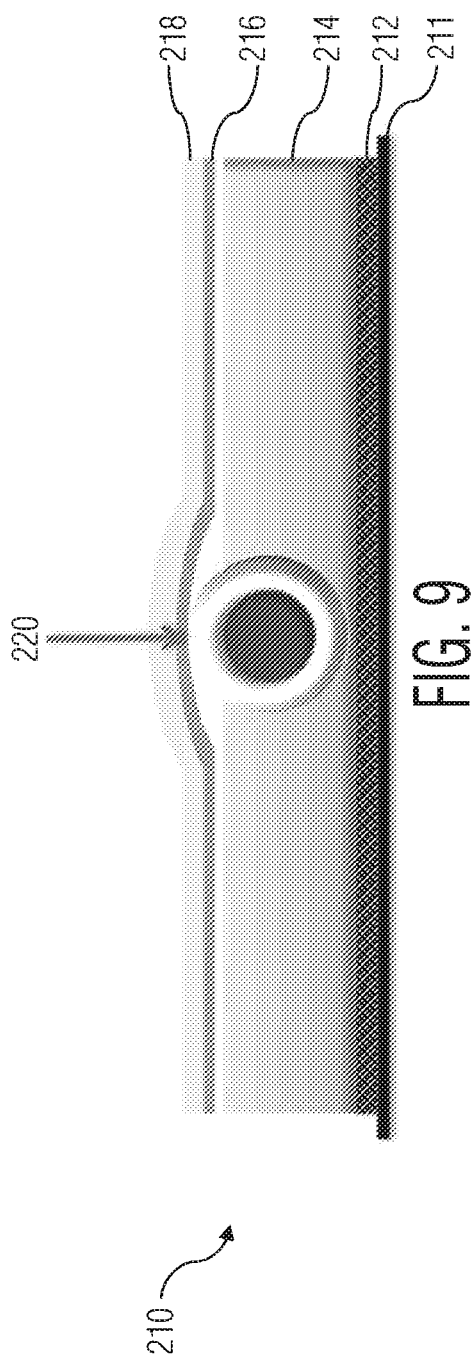
FIG. 8
FIG. 9

MEDICAL TREATMENT SIMULATION DEVICES

CROSS REFERENCE TO RELATED APPLICATIONS

This application is a U.S. National Phase Application of PCT International Application PCT/US2015/060889, filed Nov. 16, 2015, which claims priority to U.S. Patent Application No. 62/080,439, filed Nov. 17, 2014; to U.S. Patent Application No. 62/080,440, filed Nov. 17, 2014; to U.S. Patent Application No. 62/080,444, filed Nov. 17, 2014; to U.S. Patent Application No. 62/081,042, filed Nov. 18, 2014; to U.S. Patent Application No. 62/128,100, filed Mar. 4, 2015; and to U.S. Patent Application No. 62/145,018, filed Apr. 9, 2015, the contents of each of which are incorporated herein by reference in their entirety. This application is also a Continuation-in-Part of U.S. patent application Ser. No. 14/496,396, filed Sep. 25, 2014 and a Continuation-in-Part of U.S. patent application Ser. No. 14/466,027, filed Aug. 22, 2014, the contents of each of which are incorporated herein by reference in their entirety.

FIELD OF THE INVENTION

The present invention relates generally to medical simulations, and more particularly, to simulation devices for training care providers to provide medical treatment.

BACKGROUND OF THE INVENTION

Conventionally, the training process for nursing or medical students related to patient care and treatment may employ mannequins that do not provide realistic patient feedback. This lack of feedback makes it difficult for nursing or medical students to gain the education needed to perform proper medical treatments or care when working with actual patients. Accordingly, improved systems and devices are desired for training medical care providers to provide treatment.

SUMMARY OF THE INVENTION

Aspects of the present invention are medical treatment simulation systems and devices.

In accordance with one aspect of the present invention, an intravenous treatment simulation device is disclosed. The intravenous treatment simulation device includes an overlay, at least one tube, a reservoir, and a processor. The overlay is configured to be secured to a subject. The overlay has a needle-resistant inner layer and at least one conductive layer positioned outside of the needle resistant inner layer. The at least one tube is positioned within the overlay beneath the at least one conductive layer. The reservoir is adapted to store a fluid. The reservoir is coupled to provide the fluid to the at least one tube. The processor is coupled to the at least one conductive layer. The processor is configured to detect an insertion of a needle through the at least one conductive layer and generate a signal upon the detection of the insertion of the needle.

In accordance with another aspect of the present invention, a catheter treatment simulation device is disclosed. The catheter treatment simulation device includes an overlay, a tube, a sensor, a reservoir, a valve, and a processor. The overlay is configured to be secured to a subject. The overlay comprises an opening sized to receive a catheter. The tube is coupled with the opening in the overlay. The sensor is coupled to the tube. The sensor is operable to detect an insertion of the catheter into the tube. The reservoir is adapted to store a fluid. The reservoir is coupled to provide the fluid to the tube. The valve is positioned to control a flow of the fluid between the reservoir and the tube. The processor is coupled to the sensor. The processor is configured to detect the insertion of the catheter into the tube beyond a predetermined threshold and to open the valve upon the detection of the insertion of the catheter into the tube beyond the predetermined threshold.

In accordance with yet another aspect of the present invention, a defibrillation treatment simulation device is disclosed. The defibrillation treatment simulation device includes a housing, a display coupled to the housing, one or more input devices coupled to the housing, and a processor within the housing. The display is operable to display an image to a user. The one or more input devices are operable by the user to simulate applying a defibrillation signal to a subject. The processor is programmed to generate a signal to the user that the defibrillation signal has been applied to the subject and to display a simulated patient heart rhythm on the display.

In accordance with still another aspect of the present invention, a thoracic treatment simulation device is disclosed. The thoracic treatment simulation device includes an overlay, a reservoir, a motor, and a processor. The overlay is configured to be secured to a subject. The overlay covers at least a portion of a torso of the subject and comprises an opening. The reservoir is coupled with the opening. The motor is coupled to the reservoir. The motor is operable to periodically pump air into and out of the reservoir via the opening. The processor is coupled to the motor. The processor is configured to operate the motor to pump the air into and out of the reservoir in accordance with a simulated breathing pattern of the subject.

In accordance with yet another aspect of the present invention, a device for facilitating simulating performance of medical procedure on a live subject is disclosed. The device includes an overlay, a simulated treatment structure, at least one feedback device, and at least one processor. The overlay is configured to be secured to the live subject and to cover at least a portion of a body of the live subject. The simulated treatment structure is configured to simulate a structure associated with the medical procedure. The at least one feedback device is configured to provide a feedback signal to the live subject. The at least one processor is connected to the simulated treatment structure and the at least one feedback device. The processor is programmed to operate the feedback device to provide the feedback signal based upon input generated from interaction between a treatment provider and the simulated treatment structure.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. This emphasizes that according to common practice, the various features of the drawings are not drawn to scale unless otherwise indicated. On the contrary, the dimensions of the various features may be expanded or reduced for clarity. Included in the drawings are the following figures:

FIGS. 6A and 6B are diagrams illustrating an exemplary surface layer of the medical of the medical treatment simulation device of FIG. 1;

FIG. 8 is a diagram illustrating an exemplary intravenous treatment simulation device in accordance with aspects of the present invention;

FIG. 9 is a diagram illustrating a cross-section of an overlay of the intravenous treatment simulation device of FIG. 8;

DETAILED DESCRIPTION OF THE INVENTION

Aspects of the invention are described herein with reference to simulating specific medical treatments. However, it will be understood by one of ordinary skill in the art that the exemplary devices described herein may be used to simulate treatment of a variety of medical conditions, and is not limited to any particular treatment disclosed herein. Other medical treatments suitable for simulation with the disclosed devices will be known to one of ordinary skill in the art from the description herein.

The exemplary devices disclosed herein may be particularly suitable for providing an enhanced level of feedback to the medical care provider relative to conventional training devices. Audio and/or haptic feedback may be provided to the care provider during treatment in order to reinforce proper techniques. Likewise, this feedback may be provided to correct treatment errors that the care provider may otherwise struggled to detect during the simulated treatment. The provision of feedback using the exemplary devices of the present invention may desirably improve the ability of medical care providers to comfortably and effectively treat patients.

Exemplary Tracheostomy Treatment Simulation Device

Figure 1:
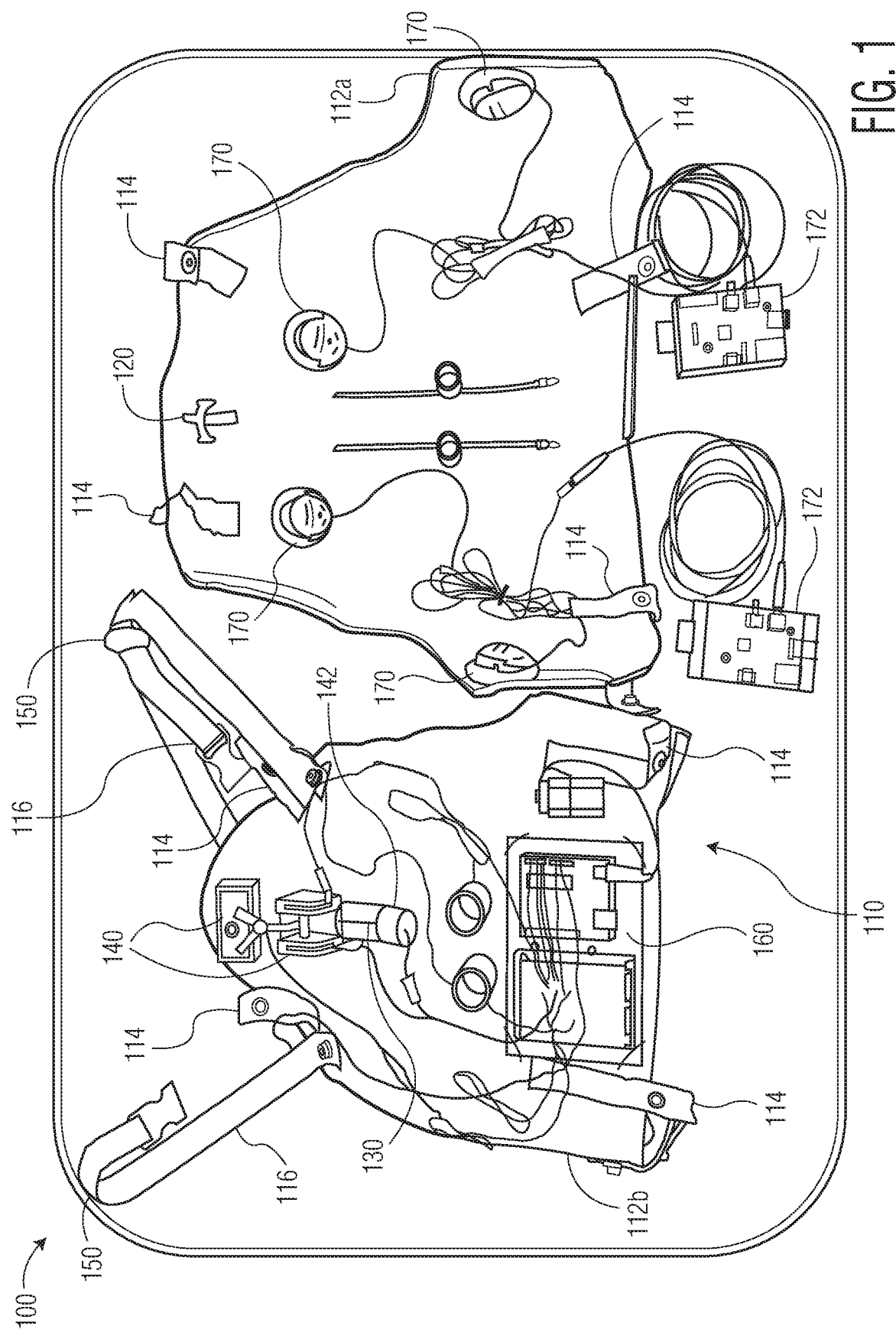
FIG. 1 is an image illustrating an exemplary medical treatment simulation device in accordance with aspects of the present invention.

With reference to the drawings, FIG. 1 illustrates an exemplary medical treatment simulation device 100 in accordance with aspects of the present invention. Device 100 is usable to train medical care providers to treat tracheostomy patients. In general, device 100 includes an overlay 110, a tracheostomy structure 120, one or more tubes 130, at least one sensor 140, and at least one feedback device 150. Additional details of device 100 are described below.

Figure 2:
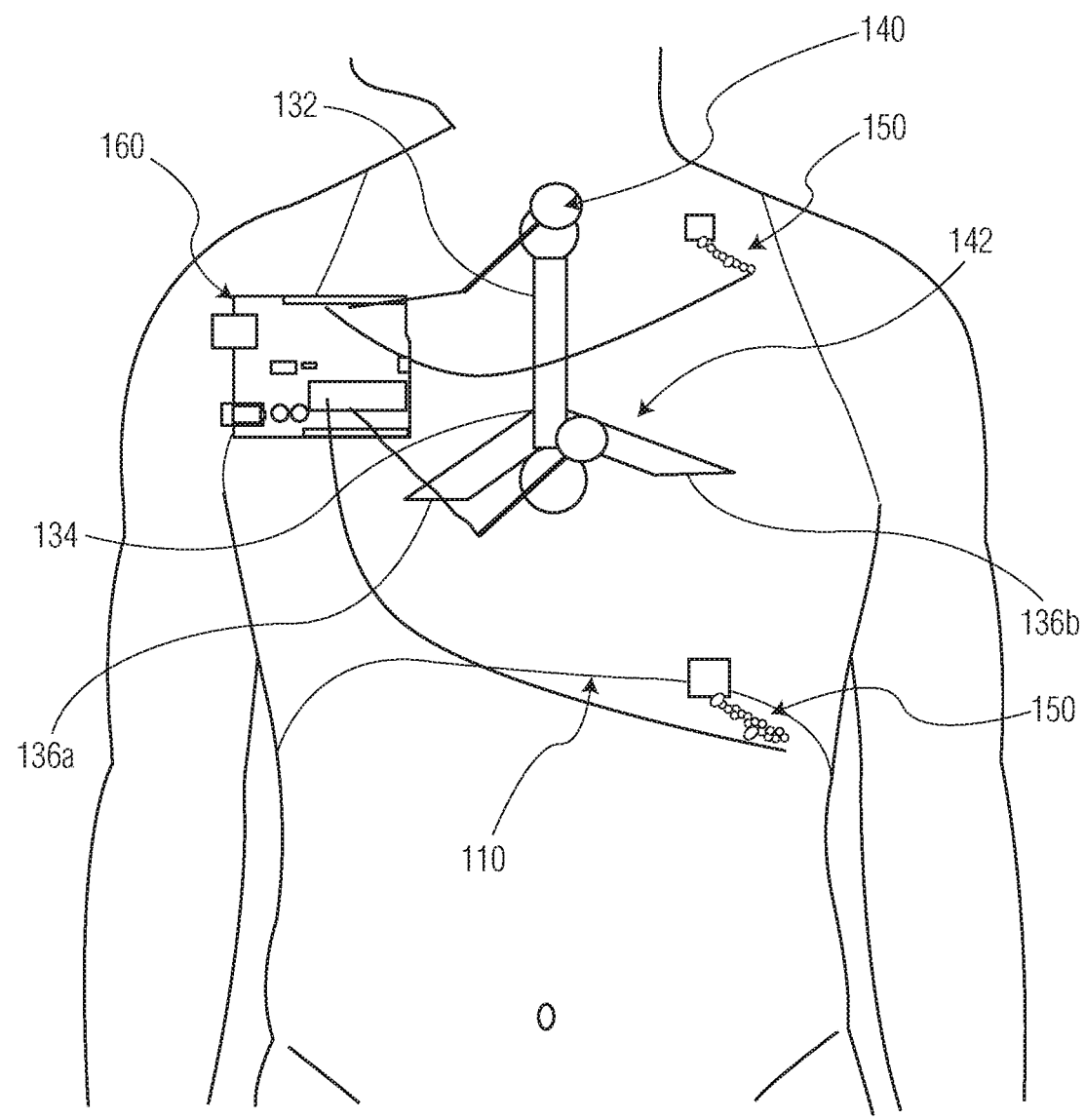
FIG. 2 is a diagram illustrating an exemplary sensor layout of the medical treatment simulation device of FIG. 1 relative to a human subject.
Figure 3:
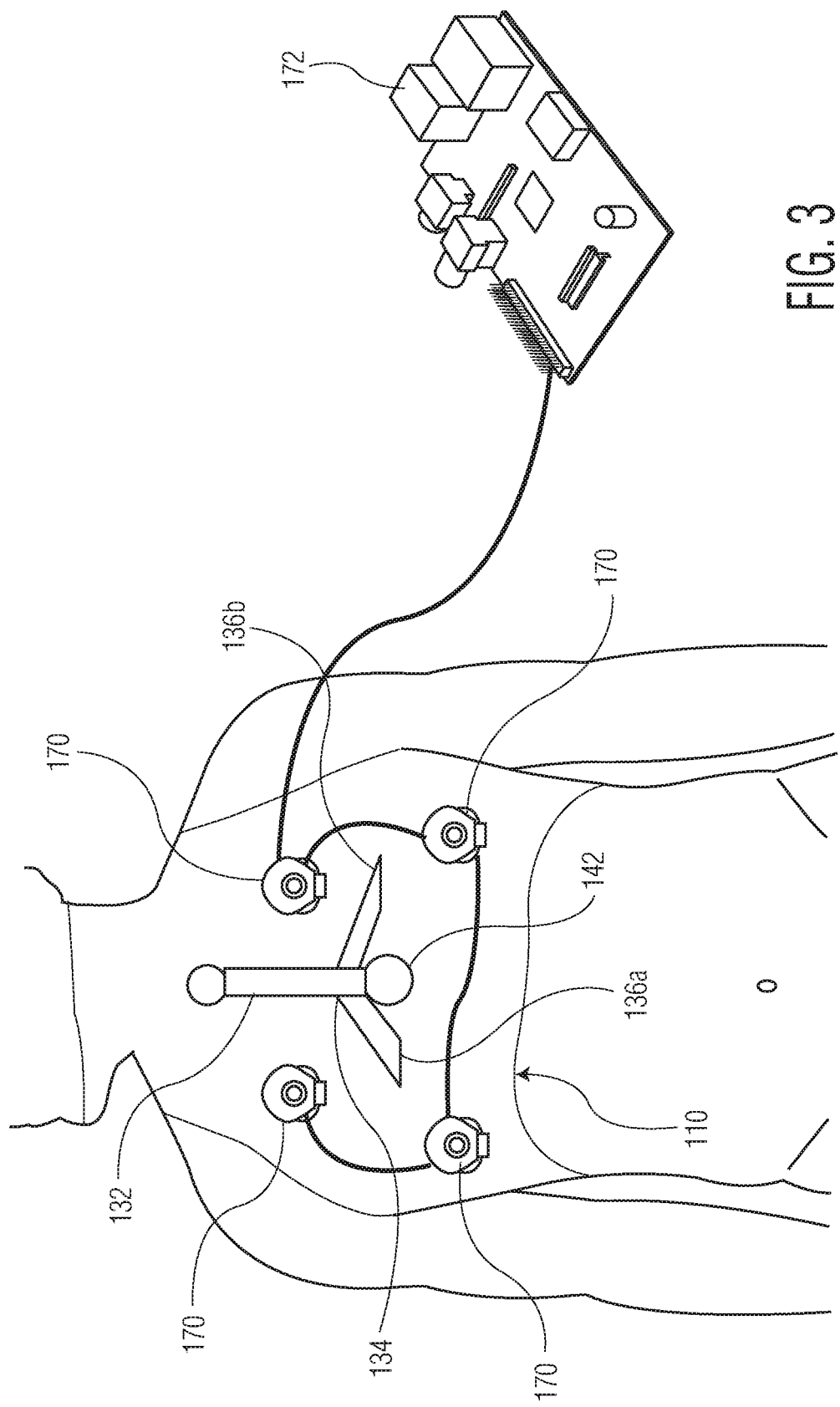
FIG. 3 is a diagram illustrating an exemplary audio feedback layout of the medical treatment simulation device of FIG. 1 relative to a human subject.

Overlay 110 is configured to be secured to a subject who is playing the role of the patient. When secured to the subject, overlay 110 is configured to cover the subject's neck and upper torso. In an exemplary embodiment, overlay 110 is shaped like a patient's neck and upper torso, as shown in FIGS. 1-3. Shaping overlay 110 as described above desirably limits the size of overlay 110, and allows the profile of overlay 110 to closely conform to the body of the subject, thereby allowing the subject to portray a tracheostomy patient.

Overlay 110 may be formed from multiple pieces that connect to define an enclosure for the components of device 100. In an exemplary embodiment, overlay 110 is a housing formed from a front shell 112a and a rear shell 112b, as shown in FIG. 1. FIG. 1 shows the inside surfaces of both front shell 112a and rear shell 112b. Front shell 112a is configured to be removably connected to rear shell 112b to form overlay 110. Shells 112a and 112b may be attached, for example, by straps, buttons, snaps, or any other structures known in the art. In an exemplary embodiment, shells 112a and 112b are attached via snaps 114 provided at the upper and lower ends of the shells 112a and 112b.

In an exemplary embodiment, overlay 110 may be formed from three separate components designed to best simulate the body of a tracheostomy patient. The pieces include the attachable hard shells 112a and 112b, a soft and pliable front surface material intended to simulate the patient's skin ("artificial skin"), and a soft back surface material for providing comfort to the subject wearing overlay 110. The operational components of device 100 (e.g. sensors and feedback devices) are provided within the hard shells of overlay 110, which thereby provides protection for these components and helps conceal wiring and other items.

An exemplary embodiment of the artificial skin layer 180 is shown in FIGS. 6A and 6B. The artificial skin layer 180 may include sound dampening material 181 in order to dampen sounds generated within overlay 110, as will be discussed below in greater detail. The artificial skin may further provide layers of materials on the outside of one or both of hard shells 112a and 112b for simulating the patient's body. In an exemplary embodiment, the layers of material include memory foam 182, PVC 183, and a nylon elastane layer 184. Alternatively, the artificial skin may comprise silicone, with an interior layer of memory foam positioned adjacent the subject's body for comfort. It will be understood that the selection, order, and thickness of layers of artificial skin layer 180 shown in FIG. 6B is provided for the purpose of illustration, and is not intended to be limiting.

Other suitable materials for use in simulating a patient's skin will be generally known to one of ordinary skill in the art from the description herein.

The layers of artificial skin 180 may be attached to the edges of the hard shells of overlay 110 via one or more attachment mechanisms. Suitable attachment mechanisms include, for example, hook-and-loop fasteners 185, anchors 186, adhesives, or double-sided tape 187, as shown in FIG. 6A. Other suitable attachment mechanisms will be known to one of ordinary skill in the art from the description herein.

Rear shell 112b further includes a plurality of straps 116 for securing overlay 110 to a subject. In an exemplary embodiment, rear shell 112b includes a pair of straps configured to encircle the subject's shoulders, as shown in FIG. 1. Straps 116 are usable to secure device 100 to the subject during the simulated treatment. Rear shell 112b may further include a foam layer on the rear thereof, in order to improve the comfort of the subject wearing overlay 110.

It will be understood by one of ordinary skill in the art that rear shell 112b may be omitted. In such an embodiment, straps may extend from front shell 112a, and the interior components of overlay 110 may all be coupled to front shell 112a.

Tracheostomy structure 120 is provided on overlay 110. Structure 120 is designed to simulate the structures implanted in an actual tracheostomy patient. Accordingly, structure 120 is provided on the neck portion of overlay 110. In an exemplary embodiment, structure 120 includes a tracheostomy faceplate 122, and a tracheostomy tube 124 attached thereto. A suitable tracheostomy structure 120 for use with the present invention is provided in FIG. 4 for the purpose of illustration.

While in this embodiment structure 120 relates to tracheostomy treatment, it will be understood that the invention is not so limited. Other suitable structures for simulating medical treatments will be known to one of ordinary skill in the art from the description herein.

Tubes 130 are positioned within overlay 110, and connected to tracheostomy structure 120. Tubes 130 are designed to simulate the airways of an actual tracheostomy patient. Accordingly, tubes 130 have a shape and size corresponding to the bronchial tubes of a patient. In an exemplary embodiment, tubes 130 include a first length of tubing 132 leading to a bifurcation 134, and a pair of tubes 136a and 136b extending from the bifurcation. An exemplary layout of tubes 130 within overlay 110 is shown by diagram in FIGS. 2 and 3. During the simulated medical treatment, the care provider may be asked to insert a suction tube through tracheostomy structure 120 and into tubes 130, in order to simulate drainage of a patient's lungs 130.

Sensor 140 is coupled to tracheostomy structure 120. Sensor 140 detects any manipulation of tracheostomy structure 120 during the simulated treatment of the subject. Examples of manipulations of tracheostomy structure 120 are set forth below.

Figure 4:
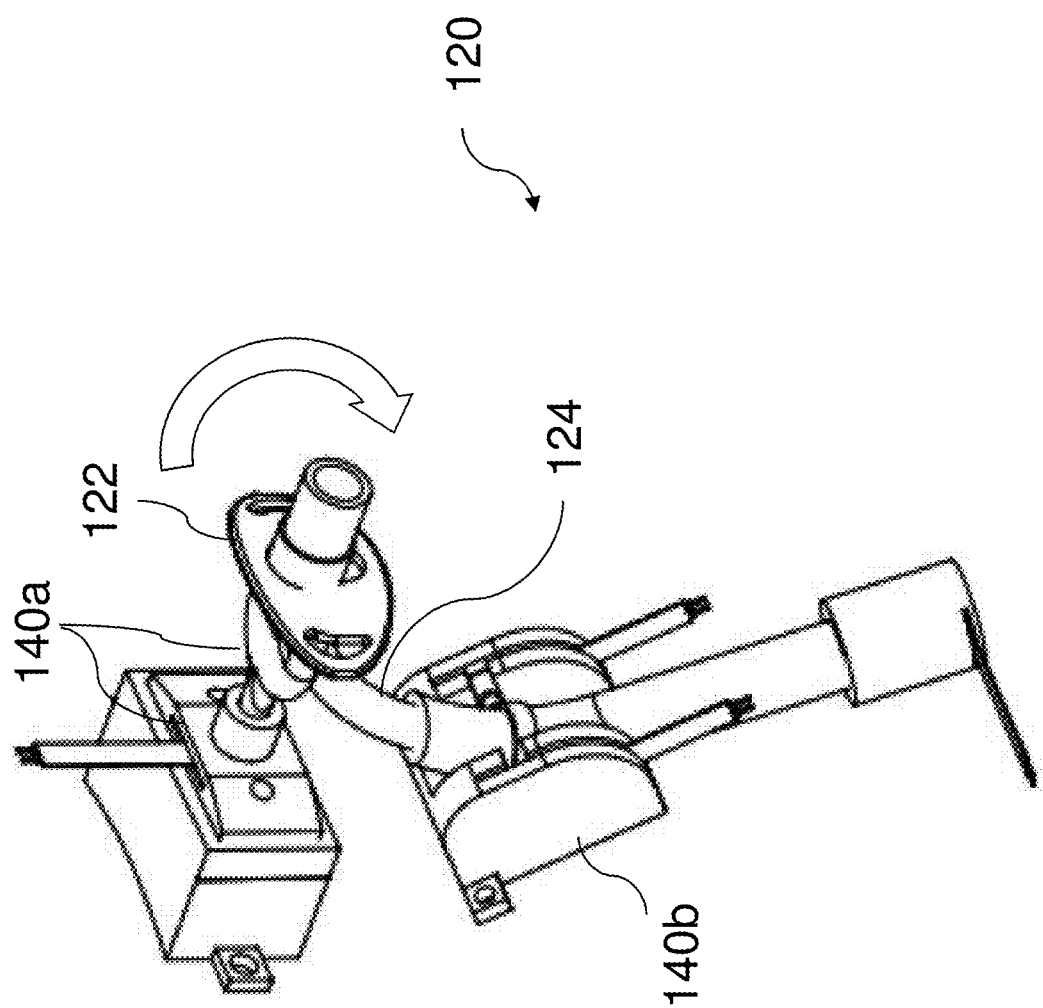
FIG. 4 is an image illustrating an exemplary tracheostomy structure and sensor layout of the medical treatment simulation device of FIG. 1.

In one exemplary embodiment, the sensor includes a normal force sensor 140a. In this embodiment, sensor 140a is configured to detect a force on tracheostomy structure 120 during the simulated treatment. The force may be a force normal to the tracheostomy structure (e.g., normal to tracheostomy faceplate 122 in FIG. 4). Sensor 140a may be an electrical force sensor positioned behind tracheostomy faceplate 122 and configured to detect a normal force on tracheostomy faceplate 122, as shown in FIG. 4. In actual tracheostomy patients, excessive force on a tracheostomy faceplate (e.g., a normal force in excess of 2 lbs.) can be a source of discomfort. Accordingly, the detection of force on tracheostomy structure 120 may be desirable in order train care providers to limit excessive force on structure 120 and prevent discomfort in actual patients.

In the above embodiment, the force sensors used are force-sensitive resistors (FSRs). FSRs are dynamic resistors that have nearly infinite resistance when no force is applied. The resistivity of the FSR decreases, non-linearly, as the force applied increases. In this embodiment, the voltage measured across the sensor may be converted into a detection of an applied force on tracheostomy structure 120.

In another exemplary embodiment, the sensor includes a rotation sensor 140b. In this embodiment, one or more force sensors 140b are configured to detect a rotation of tracheostomy structure 120 during the simulated treatment. The rotation of tracheostomy structure 120 may be an axial rotation of tracheostomy faceplate 122, as shown by a block arrow in FIG. 4. Sensor 140b may include a pair of force sensors positioned on opposed rotatable projections behind tracheostomy faceplate 122, as shown in FIG. 4, such that rotation of the faceplate 122 in either direction provides a force on the adjacent force sensor. The amount of rotation of the tracheostomy faceplate 122 may be measured by determining the corresponding force detected by sensor 140b (which increases in a determinable manner as rotational displacement increases). In actual tracheostomy patients, as with force, excessive rotation of a tracheostomy faceplate (e.g., an axial rotation in excess of 4 degrees) can also be a source of discomfort. Accordingly, the detection of rotation of tracheostomy structure 120 may be desirable in order train care providers to limit excessive rotation on structure 120 and prevent discomfort in actual patients.

Figure 5:
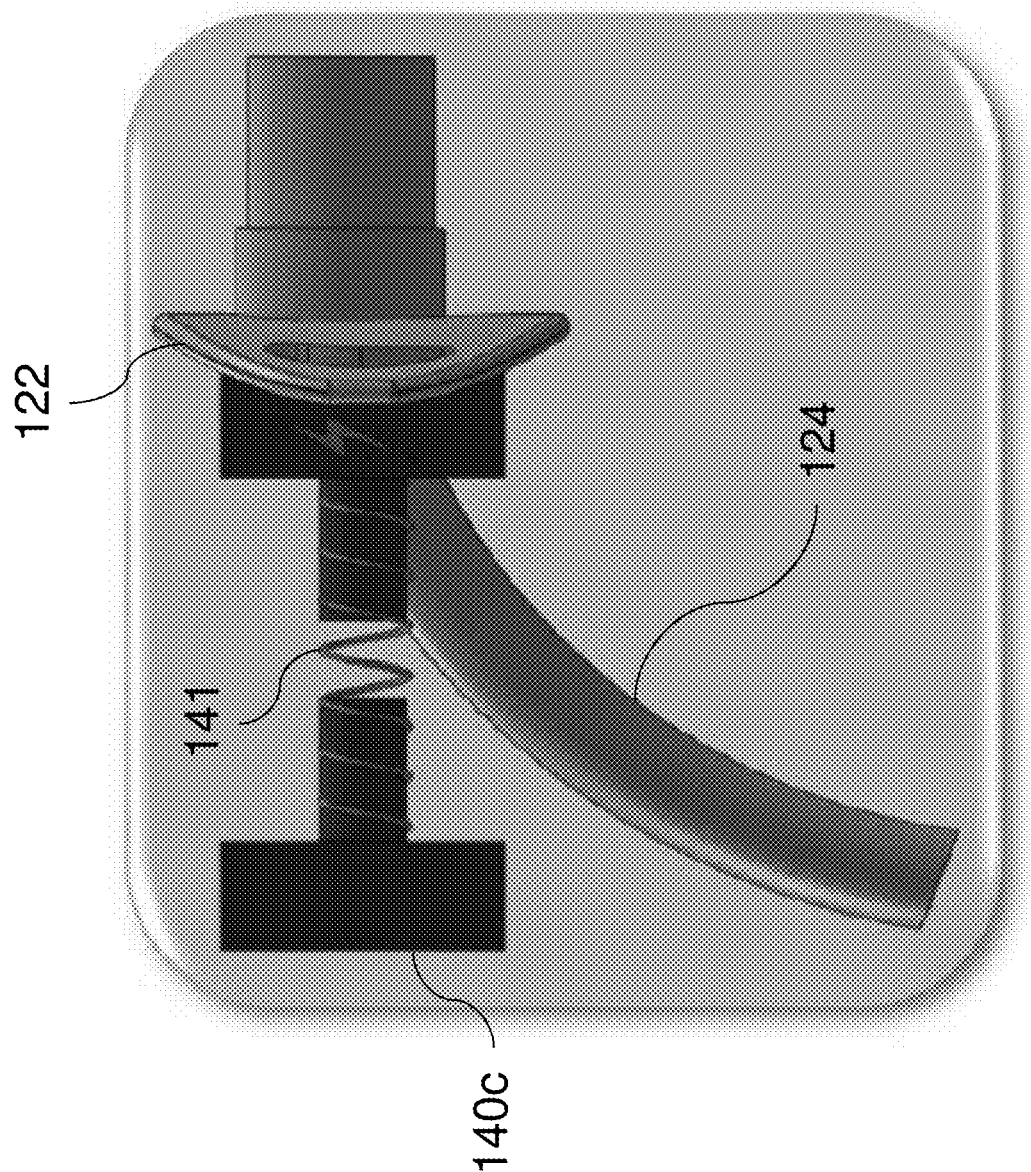
FIG. 5 is an image illustrating an alternative exemplary tracheostomy structure and sensor layout of the medical treatment simulation device of FIG. 1.

In another exemplary embodiment, the sensor includes a spring-based sensor 140c. In this embodiment, the spring-based sensor 140c is configured to detect a force on tracheostomy structure 120 during the simulated treatment. The force may be a force normal to the tracheostomy structure (e.g., normal to tracheostomy faceplate 122 in FIG. 5). Sensor 140c may be a mechanical force sensor that is configured to detect a normal force on tracheostomy faceplate 122 as that force is transmitted through a spring 141 coupled to tracheostomy faceplate 122, as shown in FIG. 5. For example, the sensor may include an electric circuit that is kept open by a spring having a spring constant that corresponds to the response of a human throat. When the force threshold is exceeded, the circuit closes, thereby signaling excessive force received by the tracheostomy structure 120. Coupling of tracheostomy structure 120 to a spring-based sensor as shown in FIG. 5 may be desirable in order to provide realistic movement of tracheostomy structure 120 during the simulated treatment by the care provider.

The spring-based sensor 140c may further include a circuit that is adapted to be closed during excessive force on tracheostomy structure 120. In an exemplary embodiment, the spring-based sensor 140c includes circuit contacts that are spaced a predetermined distance apart by spring 141. When an excessive force is applied to tracheostomy faceplate 122 (for example), spring 141 is compressed, and the circuit contacts are closed. Closing of the circuit contacts may function to automatically operate one or more feedback device 150, so that feedback is provided as soon as the excessive force is detected.

In addition to providing one or more sensors 140 coupled to tracheostomy structure 120, device 100 may further include one or more sensors 142 coupled to tubes 130. In an exemplary embodiment, sensor 142 is a force sensor coupled to tubes 130 to detect any contact between an inserted suction tube and the inner wall of tubes 130 during the simulated treatment. In a particularly preferred embodiment, sensor 142 is a force sensor coupled to the bifurcation 134 of tubes 130 to detect contact with the bifurcation 134, where contact with the bifurcation 134 is determined to be any force above a predetermined amount (e.g., in excess of 0.5 lbs.). In actual tracheostomy patients, such contact with the patient's bronchial tubes can cause irritation. Accordingly, the detection of contact on bifurcation 134 may be desirable in order train care providers to limit such contact and provide effective treatment to tracheostomy patients.

The above examples of types and locations of sensors 140 are provided for the purposes of illustration, and are not intended to be limiting. It will be understood that any combination of the disclosed sensors may be used, and that additional types and locations of sensors may be used, without departing from the scope of the invention. Other possible sensors for use in device 100 would be known to one of ordinary skill in the art.

Feedback device 150 is also coupled to overlay 110. Feedback device 150 is configured to provide feedback to the user of device 100 (i.e. the care provider) based on the manipulation detected by sensor 140. Feedback may be provided when the manipulation detected by sensor 140 exceeds a predetermined threshold. For example, feedback may be provided to the user when the force on tracheostomy structure 120 exceeds a predetermined limit, or when tracheostomy structure 120 is rotated more than a predetermined amount. Additionally, feedback may be provided to the user when contact of tubes 130 is detected.

In an exemplary embodiment, feedback device 150 is a vibrating motor. The vibrating motor creates a vibration of overlay 110 that can be felt by the user during the simulated treatment of the subject. Suitable vibrating motors for use as feedback device 150 include, for example, a shaftless vibration motor provided by Precision Microdrives (Model 310-101; Size 10 mm).

In another exemplary embodiment, feedback device 150 is an audible alarm. The alarm generates a sound that can be heard by the user during the simulated treatment of the subject. Suitable loudspeakers for use as the audible alarm will be known to one of ordinary skill in the art from the description herein. Other feedback devices, or combinations thereof, will be known to one of ordinary skill in the art from the description herein.

In addition to or alternatively to providing feedback to the care provider, feedback device 150 may also provide feedback to the subject wearing device 100. In an exemplary embodiment, feedback devices 150 may be coupled to straps 116 of overlay 110, in order to provide feedback (e.g., vibration feedback) only to the subject, as shown in FIG. 1. Such feedback may be used as a signal to cause the subject to respond to the simulated treatment in a predetermined way, without directly indicating to the care provider that improper or undesirable treatment has been provided.

Where multiple sensors 140 are employed by device 100, it may be desirable to provide different types of feedback dependent on the information being detected. For example, device 100 may be configured to provide vibration feedback when excessive force or rotation is provided on tracheostomy structure 120, and may be configured to provide audible feedback when contact occurs in tubes 130.

In an exemplary embodiment, each sensor employed by device 100 may have its own feedback device 150 provided in a particular location or type (e.g., in each strap 116), in order for the user and/or the subject to determine which sensor has been triggered during the simulated treatment. For example, sensor(s) 140 for the tracheostomy structure 120 may include a feedback device 150 in the left strap 116, and sensor 142 for the tubes 130 may include a feedback device 150 in the right strap 116. Other possible combinations of sensor detection and feedback will be apparent to one of ordinary skill in the art from the description herein.

Device 100 is not limited to the above-described components, but can include alternate or additional components as would be understood to one of ordinary skill in the art in view of the examples below.

For example, device 100 may include a microcontroller 160. In an exemplary embodiment, microcontroller 160 is connected in communication with sensors 140 and feedback device 150. Microcontroller 160 processes the information detected by sensors 140, and determines whether the sensed manipulations (force, rotation, etc.) exceed predetermined thresholds stored by microcontroller 160. If microcontroller 160 determines that any threshold is exceeded, it sends signals to operate feedback device 150 to provide feedback to the user of device 100.

For another example, device 100 may include one or more speakers 170. Speakers 170 are positioned within overlay 110, and are configured to emit sounds during the simulated treatment of the subject. The care provider may be trained to listen for sounds (e.g., noises within a patient's lungs) during the treatment being provided. Accordingly, device 100 may include a plurality of speakers positioned within overlay 110 in locations corresponding to the areas at which the care provider is trained to listen.

An exemplary layout of speakers 170 is provided in FIG. 3. Suitable loudspeakers for use as speaker 170 include, for example, a miniature speaker provided by Visaton (Model: K 28 WP; Size: 8 ohm 2.3 cm). In this embodiment, simulated lung sounds can be auscultated in four anatomically correct regions of the overlay 110 corresponding to anterior thorax locations, in order to simulate medical conditions such as pneumonia, mucus build up in the upper airway necessitating tracheal suctioning, wheezing (constriction of the air passages in the lungs) necessitating simulated aerosolized medication administration, and finally normal lung sounds indicating treatment choice was effective. Additionally, the layout of speakers 170 could include a rear surface corresponding to the posterior thorax, in order to allow posterior lung auscultation in 4-8 lung fields and include the same options for lung sounds mentioned above.

Speakers 170 emit simulated patient sounds that the care provider would expect to hear from a patient during treatment corresponding to different medical conditions of the patient, as set forth above. Preferably, these sounds are quiet enough that they are inaudible to the care provider without the use of a stethoscope.

Speakers 170 may be connected with one or more microcontrollers 172 for controlling the sounds emitted therefrom, as shown in FIGS. 1 and 3. Microcontrollers 172 may be located with overlay 110, or may be provided remote from overlay 110. Likewise, the connection between speakers 170 and microcontrollers 172 may be wireless or wired. In an exemplary embodiment, a trainer of the care provider may control the sounds emitted from speakers 170 during the simulated medical treatment. This control may include the ability to control when speakers 170 emit sound, which speakers 170 emit sounds, what sounds are emitted, and how loud those sounds are emitted. Alternatively, microcontroller 160 may control the sounds emitted from speakers 170 in addition to the operation of feedback device 150.

Figure 7:
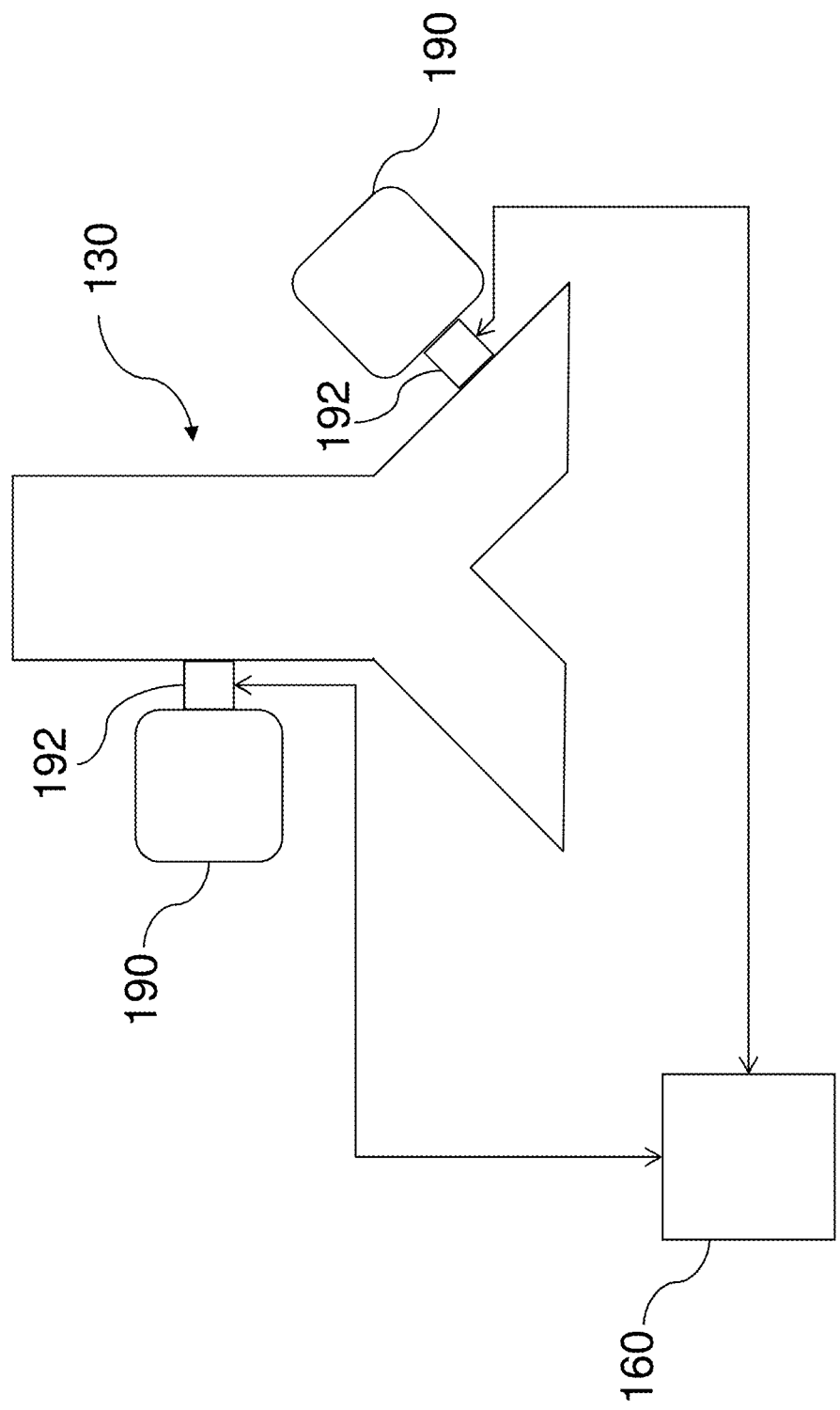
FIG. 7 is a diagram illustrating an exemplary fluid feedback system of the medical treatment simulation device of FIG. 1.

For yet another example, device 100 may include an option to simulate secretions in the airway during treatment. During actual medical treatment of a tracheostomy patient, it is possible for mucus to build up in the patient's bronchial tubes/upper airway. Such buildup may requirement suctioning or tracheostomy care to provide a realistic feel while suctioning. Accordingly, as shown in FIG. 7, device 100 may include one or more reservoirs 190 adapted to store fluid having a viscosity corresponding to the mucus found in a patient. Each of these reservoirs may include one or more valves 192 adapted to release the fluid in the one or more tubes 130. The reservoirs fluid may be released into the tubes 130 by gravity feed, or reservoirs 190 may further include one or more actuators or pumps (such as peristaltic pumps, not shown) for pushing fluid into tubes 130 during the simulated treatment of the patient. Suitable pumps and valves for use in fluid reservoirs will be known to one of ordinary skill in the art from the description herein.

Reservoirs 190 containing simulated mucus may be controlled through substantially the same systems as discussed above with respect to speakers 170. For example, the valves 192 of reservoirs 190 may be electrically coupled to and controlled by microcontroller 160 in a predetermined fashion during the course of a simulated treatment, as shown in FIG. 7. Alternatively, a trainer of the care provider may control the release of fluid from reservoirs during the simulated medical treatment using one or more microcontrollers that are wired or wirelessly connected to the fluid reservoirs.

Exemplary Intravenous Treatment Simulation Device

Figure 10:
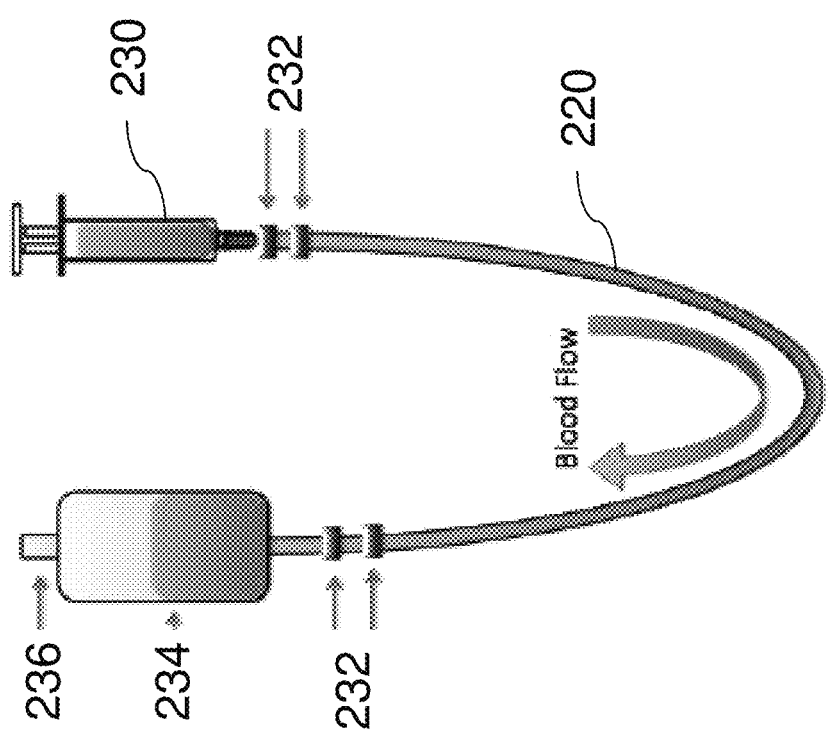
FIG. 10 is a diagram illustrating a fluid flow path of the intravenous treatment simulation device of FIG. 8.

FIGS. 8-10 illustrate an exemplary intravenous treatment simulation device 200 in accordance with aspects of the present invention. Device 200 is usable to train medical care providers to perform intravenous treatments. In general, device 200 includes an overlay 210, at least one tube 220, a reservoir 230, and a processor 240. Additional details of device 200 are described below.

Overlay 210 is configured to be secured to a subject who is playing the role of the patient. In an exemplary embodiment, overlay 210 is adapted to be worn around the subject's arm, as shown in FIG. 8. Preferably, overlay 210 can be slid onto the subject's arm in one or more pieces. Overlay 210 desirably has a thin profile, to allow overlay 210 to closely conform to the shape of the subject's arm.

Overlay 210 is formed from multiple layers. As shown in FIG. 9, overlay 210 includes a needle-resistant inner layer 212, a middle layer 214, and at least one conductive layer 216 positioned outside of inner layer 212 and middle layer 214 (relative to the subject's arm). The layers of overlay 210 are selected to promote simulation of the intravenous treatment while providing protection to the subject wearing device 200. Additional details regarding the layers of overlay 210 are set forth below.

Needle-resistant inner layer 212 prevents the subject from being inadvertently stuck with a needle during simulation of the intravenous treatment. Needle-resistant inner layer 212 may be formed from any flexible fabric or material that exhibits high resistance to needle penetration. In an exemplary embodiment, inner layer 212 is formed from SUPERFABRIC® brand materials provided by HexArmor. Alternatively, inner layer 212 may be formed from small rigid plates that flexibly overlap along the contour of the subject's arm. Other suitable materials for forming needle-resistant inner layer 212 will be known to one of ordinary skill in the art from the description herein.

Inner layer 212 may be continuous, or may be formed from patches of material positioned in locations where the intravenous treatment is expected to occur. Where inner layer 212 is not continuous, it may be coupled to a base layer 211 to provide a structure for the separate pieces that form inner layer 212. Base layer 211 may be formed from a material that contours to the subject's arm, such as SPANDEX®.

Middle layer 214 is positioned between the needle-resistant inner layer 212 and the outer conductive layer 216. Middle layer 214 stabilizes the tube 220 of device 200. Middle layer 214 may have a thickness selected based on a diameter of tube 220, such as a thickness between ½ the diameter of tube 220 up to a thickness greater than the diameter of tube 220, so that tube 220 can be at least partially or fully embedded or covered by the material of middle layer 214. To this end, middle layer 214 may have one or more channels defined therein for receiving tube 220. In an exemplary embodiment, middle layer 214 is formed from silicone rubber. Other suitable materials for forming middle layer 214 will be known to one of ordinary skill in the art from the description herein.

Conductive layer 216 is positioned outside of inner layer 212 and middle layer 214. Conductive layer 216 enables device 200 to determine when a needle has been inserted into device 200, as will be discussed below. Conductive layer 216 may be formed from any flexible conductive material or fabric. In an exemplary embodiment, conductive layer 216 is formed from a fabric containing a plurality of conductive filaments therein. Other suitable conductive fabrics will be known to one of ordinary skill in the art from the description herein.

Overlay 210 may further include an artificial skin layer 218 outside of conductive layer 216. Skin layer 218 is formed from a material selected to simulate the look and feel of a patient's skin, such as silicone. Other suitable materials will be known to one of ordinary skill in the art from the description herein.

In an exemplary embodiment, conductive layer 216 and skin layer 218 are removable from middle layer 214 during or following use of device 200. This may be preferable in order to allow tube 220 to be removed from middle layer 214 for cleaning or replacement.

Tube 220 is positioned within overlay 210 beneath conductive layer 216. In an exemplary embodiment, tube 220 is at least partially embedded in middle layer 214 in order to prevent movement of tube 220 within overlay 210. Tube 220 receives simulated blood during the simulated intravenous treatment. Tube 220 is formed from a material such as silicone that allows a needle to penetrate tube 220 during the simulated treatment. Tube 220 desirably stretches along a substantial length of overlay 210 (e.g., from the user's wrist to above the user's elbow), in order to provide multiple different needle insertion sites along the subject's arm.

Tube 220 is connected at one end to reservoir 230. Reservoir 230 is adapted to store a fluid. In operation, reservoir 230 stores simulated blood during the simulated intravenous treatment. The simulated blood may be, for example, formed from a combination of water and one or more viscous gels, lubricants, or dyes to achieve the desired amount of flow and color to simulate blood. Reservoir 230 is coupled to tube 220 in order to provide the simulated blood to tube 220.

In an exemplary embodiment, reservoir 230 is part of a syringe pump, as shown in FIG. 10. The syringe pump is adapted to apply pressure to the fluid in reservoir 230 in order to cause the fluid to flow into and through tube 220. The syringe pump may further apply pressure so that the fluid in tube 220 is under pressure during the simulated intravenous treatment. The fluid may be maintained under pressure through the use of one or more valves 232, as shown in FIG. 10. While a syringe pump is shown in FIG.

10, it will be understood that other structures may be utilized in connection with reservoir 230 to cause fluid to flow into and through tube 220. Such structures include, for example, hand pumps or peristaltic pumps.

Tube 220 may be connected at its other end to collector 234. Collector 234 collects the simulated blood that has flown through tube 220. Collector 234 may include a one-way valve to prevent fluid in collector 234 to flow back into tube 220. Collector 234 may include one or more drainage outlets 236 to allow drainage of the fluid in collector 234. In order to drain tube 220, pressure may be applied from the syringe pump when no fluid is stored in reservoir 230, in order to force air into tube 220 and cause any remaining fluid in tube 220 to be pumped into collector 234.

The connections between tube 220, reservoir 230, and collector 234 may be internal or external to overlay 210. In an exemplary embodiment, reservoir 230 and collector 234 are external to overlay 210 in order to provide simplified control over the pumping of fluid out of reservoir 230 and/or the draining of fluid from collector 234. In this embodiment, tube 220 exits overlay 210 (e.g., near the subject's should/armpit, as shown in FIG. 8) in order to be connected with reservoir 230 and collector 234.

Processor 240 is coupled to conductive layer 216. By detecting signals from conductive layer 216, processor 240 is configured to detect an insertion of a needle through conductive layer 216 during the simulated intravenous treatment. Suitable processors for use as processor 240 include, for example, ARDUINO® processors. Other suitable processing elements will be known to those of ordinary skill in the art.

An exemplary operation of processor 240 in detecting a needle insertion is described below. Conductive layer 216 has a predetermined electrical resistance, which may be monitored by processor 240 by the application of a small voltage across conductive layer 216. During insertion of a needle, the conductive fibers in layer 216 may be moved or displaced due to contact with the needle. This contact with the needle changes the electrical resistance of conductive layer 216 in a manner which may be detected by processor 240. Processor 240 may therefore sense a change in electrical resistance of conductive layer 216 in order to detect the insertion of the needle.

Alternatively, processor 240 may employ another method of detection in embodiments that include multiple conductive layers 216. In such embodiments, the multiple conductive layers 216 may be separated by an insulating layer (such as a silicone rubber layer). During insertion of a metal needle, the needle creates a short circuit between the conductive layers 216. Processor 240 may detect this short circuit by application of a small voltage to one of the conductive layers 216. Processor 240 may therefore sense a short circuit between multiple conductive layers 216 in order to detect the insertion of the needle.

Regardless of the method of detection, processor 240 is further configured to generate a signal upon detection of the insertion of the needle. This signal is provided to the subject wearing device 200, in order to prompt the subject to simulate or act in the role of a patient who has been stuck with a needle. The actions or statements performed by the subject may be predetermined by the subject or by one or more persons responsible for the simulation.

In an exemplary embodiment, processor 240 is electrically connected to a feedback device 250. Feedback device 250 may be any of the devices discussed above with respect to feedback device 150. In a preferred embodiment, feedback device 250 is a tactile signal generator, such as a vibrating motor. In this embodiment, processor 240 is configured to actuate the vibrating motor to provide a tactile signal to the subject upon detection of the insertion of the needle. This signal is preferably provided in real time, so that the subject can simulate the role of the patient as the needle is inserted into device 200.

Processor 240 may be positioned with overlay 210, or may be external to overlay 210. In either embodiment, processor 240 may include one or more wires 242 for connection with conductive layer 216 and/or feedback device 250. Feedback device 250 may preferably be positioned away from overlay 210, so that the user performing the simulated intravenous treatment cannot tell that a tactile signal has been provided to the subject. In an exemplary embodiment, feedback device 250 may be coupled to the subject's torso or opposite arm, and may receive signals from processor 240 through one or more wires exiting overlay 210 adjacent the subject's shoulder or armpit.

Exemplary Catheter Treatment Simulation Device

Figure 12:
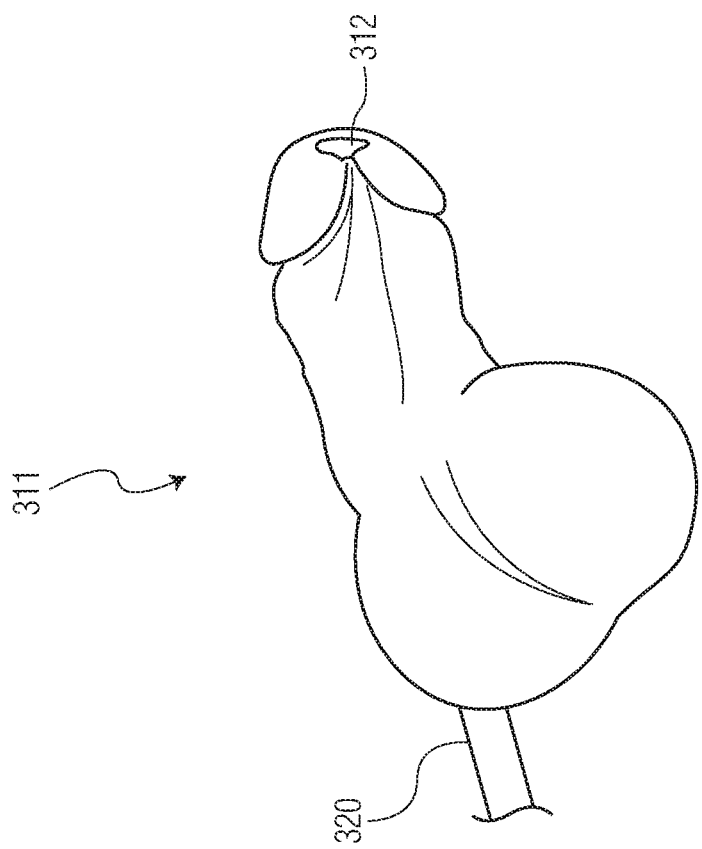
FIG. 12 is an image illustrating genitalia of the exemplary catheter treatment simulation device of FIG. 11.
Figure 11:
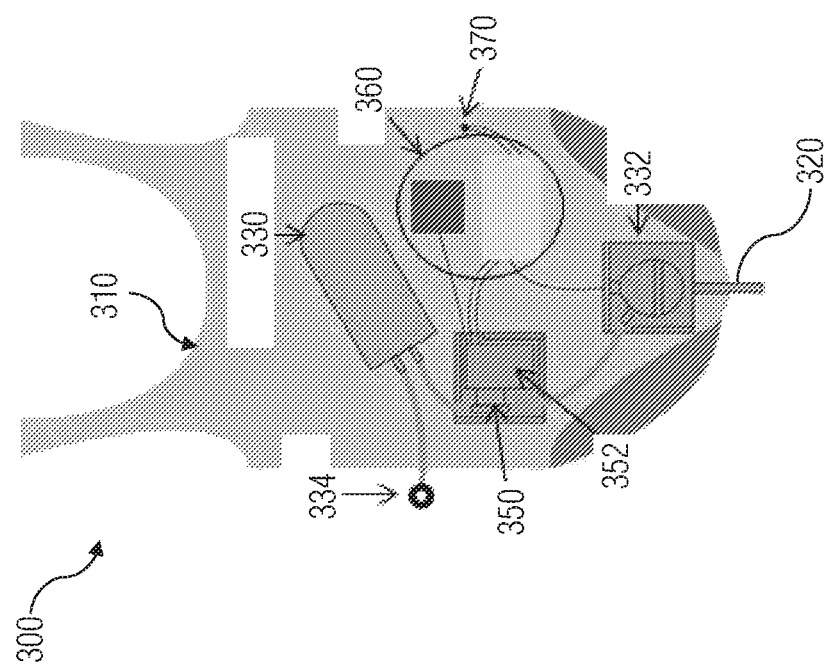
FIG. 11 is a diagram illustrating an exemplary catheter treatment simulation device in accordance with aspects of the present invention.

FIGS. 11-13 illustrate an exemplary catheter treatment simulation device 300 in accordance with aspects of the present invention. Device 300 is usable to train medical care providers to perform catheterization treatments, such as urinary catheterization. In general, device 300 includes an overlay 310, a tube 320, a reservoir 330, a sensor 340, a valve 350, and a processor 360. Additional details of device 300 are described below.

Overlay 310 is configured to be secured to a subject who is playing the role of the patient. In an exemplary embodiment, overlay 310 is adapted to be worn to cover the lower portion of the subject's torso, as shown in FIG. 11. Overlay 310 desirably has a thin profile, to allow overlay 310 to closely conform to the shape of the subject. Overlay 310 may include any of the layers described above with respect to overlays 110 and 210 in order to better simulate the appearance and feel of a patient.

Where device 300 is intended to simulate urinary catheterization, at least a portion 311 of overlay 310 is shaped to simulate genitalia of the subject. An exemplary portion of overlay 310 shaped to correspond to the genitalia of a male subject is shown in FIG. 12. This portion of overlay 310 includes an opening 312 sized to receive a catheter during the simulated catheterization.

Tube 320 is coupled with the opening 312 in overlay 310. Tube 320 receives the catheter during the simulated catheterization. Tube 320 is formed from a material such as silicone that allows it to flex and expand during the simulated treatment.

Tube 320 is connected at one end to reservoir 330. Reservoir 330 is adapted to store a fluid. In operation, reservoir 330 stores simulated urine during the simulated catheterization. The simulated urine may be, for example, formed from a combination of water and one or more viscous gels, lubricants, or dyes to achieve the desired amount of flow and color to simulate urine.

Reservoir 330 is coupled to tube 320 in order to provide the simulated urine to tube 320. In an exemplary embodiment, reservoir 330 is coupled to a compartment 332 in communication with tube 320.

In a preferred embodiment, reservoir 330 is positioned immediate beneath an outer surface of overlay 310 adjacent the portion shaped to simulate genitalia. In this region, reservoir 330 may simulate the subject's bladder. This may desirably enable the user performing the simulated catheterization to palpate or scan reservoir 330 to determine that reservoir 330 contains fluid, and that the subject should be catheterized.

Sensor 340 is coupled to tube 320. Sensor 340 may be positioned within compartment 332, e.g., in a path of insertion of the catheter. Sensor 340 is operable to detect insertion of the catheter. Sensor 340 communicates with processor 360 to determine when the catheter has been inserted beyond a predetermined threshold. The predetermined threshold may, for example, be based on a distance of insertion of the catheter or a force of insertion exerted by the catheter.

Figures 13A, 13B:
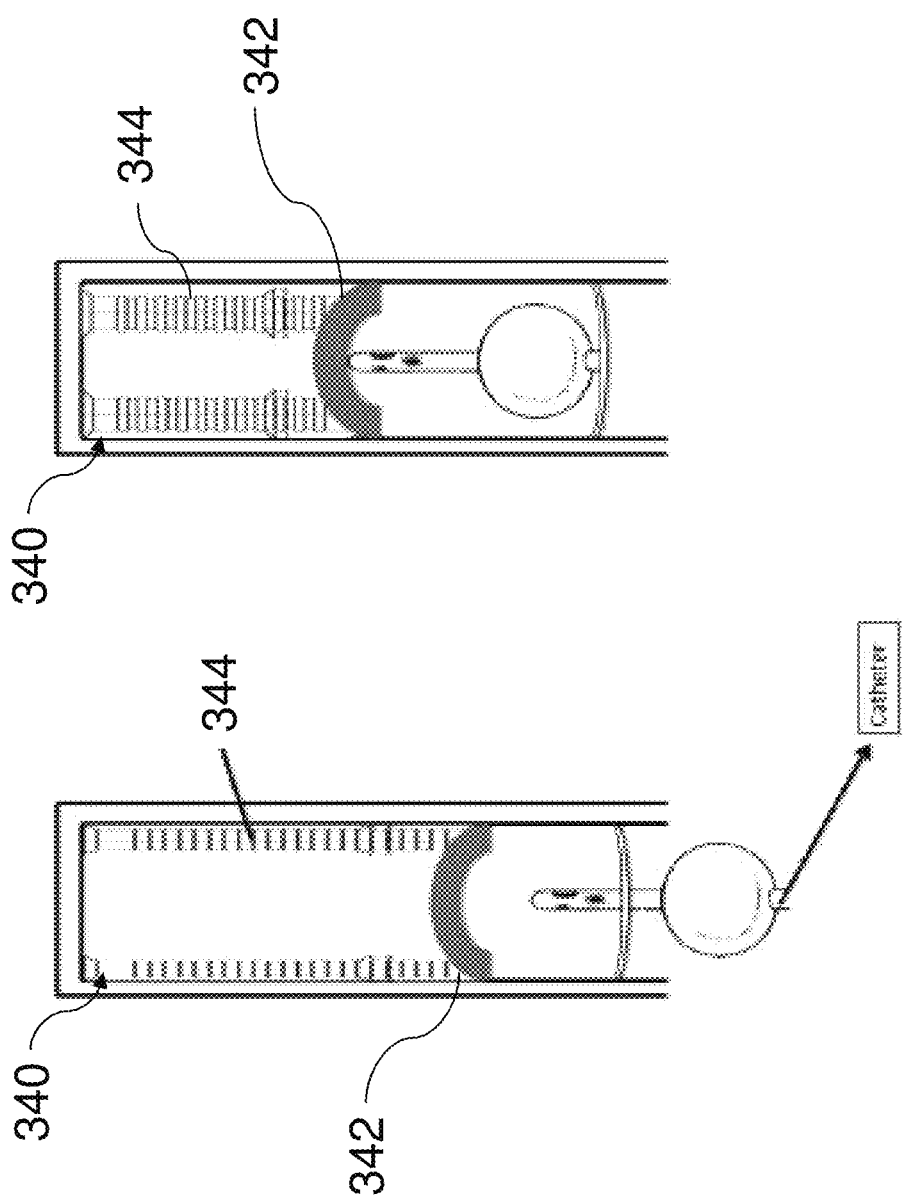
FIGS. 13A and 13B are diagrams illustrating a force sensor of the exemplary catheter treatment simulation device of FIG. 11 in uncompressed and compressed configurations, respectively.

In an exemplary embodiment, sensor 340 senses a force exerted by the catheter during insertion. In this embodiment, sensor 340 is in force communication with a plate 342 positioned to be contacted by the catheter during insertion, as shown in FIGS. 13A and 13B. Plate 342 may be coupled to a spring 344, and is moved linearly against the biasing force of spring 344 by the catheter during insertion. The base of spring 344 may then be coupled to sensor 340. During insertion, sensor 340 detects the force on plate 342 via the compression of spring 344, and transmits the detected force to processor 360. The predetermined force may be, for example, an amount of force necessary to cause a catheter to enter a human bladder during conventional catheterization.

In an alternative embodiment, sensor 340 senses when the catheter has been inserted a predetermined distance. In this embodiment, sensor 340 may comprise an optical or light sensor configured to detect when the catheter has reached a predetermined position within tube 320. The predetermined positioned may be, for example, an area of connection between tube 320 and reservoir 330 or compartment 332. Sensor 340 may then send a signal to processor 360 when the catheter has been inserted to the predetermined distance.

In another alternative embodiment, sensor 340 detects a change in the diameter of tube 320 to determine when the catheter has been inserted. Sensor 340 may detect the change in diameter at opening 312 to detect initial insertion, or may detect the change in diameter at a predetermined point along tube 320, such as the area of connection between tube 320 and reservoir 330. Sensor 340 may detect the change in diameter of tube 320 using one or more flex sensors positioned contacting the outer circumference of tube 320. Sensor 340 may then send a signal to processor 360 when the catheter has been inserted.

Valve 350 is positioned to control a flow of the fluid between reservoir 330 and tube 320. Valve 350 may be positioned within either tube 320 or reservoir 330, or may be positioned within a separate tube or other structure connecting reservoir 330 and tube 320. Valve 350 is in communication with processor 360, such that valve can be actuated (opened or closed) by processor 360. In an exemplary embodiment, valve 350 is a twist valve.

When valve 350 is opened, fluid flows out of reservoir 330 toward tube 320. The fluid may flow through valve 350 under the force of gravity, or under pressure. In an exemplary embodiment, device 300 includes a pressurizing element 334 coupled to reservoir 330 to propel the fluid within reservoir 330 through valve 350 toward tube 320. The fluid flows from reservoir 330 into compartment 332. As fluid fills compartment 332, it begins to enter the catheter under pressure from gravity and/or a pressurizing element. The fluid then flows out of device 300 within the catheter as part of the simulated catheterization treatment. Suitable elements for use as pressurizing element 334 include, for example, peristaltic pumps and/or syringe pumps.

In addition to valve 350, device 300 may also include a separate valve for reservoir 330 in order to prevent leakage from reservoir 330 within overlay 310. In this embodiment, reservoir 330 may be configured to be removed from overlay 310, e.g., for thorough cleaning and drying.

Processor 360 is coupled to sensor 340. Processor 360 is configured to detect when the catheter has been inserted into tube 320 beyond the predetermined threshold (e.g., the force or distance thresholds described above). Processor 360 is further configured to actuate valve 350 to allow fluid out of reservoir 330 and into the catheter when processor 360 detects insertion of the catheter beyond the predetermined threshold, as described above. Where valve 350 is a twist valve, processor 360 may operate a motor 352 configure to twist the valve between opened and closed positions.

Processor 360 is further configured to generate a signal upon detection of the insertion of the catheter beyond the predetermined threshold. This signal is provided to the subject wearing device 300, in order to prompt the subject to simulate or act in the role of a patient being catheterized. The actions or statements performed by the subject may be predetermined by the subject or by one or more persons responsible for the simulation.

In an exemplary embodiment, processor 360 is electrically connected to a feedback device 370. Feedback device 370 may be any of the devices discussed above with respect to feedback devices 150 and 250. In a preferred embodiment, feedback device 370 is a tactile signal generator, such as a vibrating motor coupled to the subject in a position where the subject can feel the vibration, such as within overlay 310. In this embodiment, processor 360 is configured to actuate the vibrating motor to provide a tactile signal to the subject upon detection of the insertion of the catheter beyond the predetermined distance. This signal is preferably provided in real time, so that the subject can simulate the role of the patient, e.g., upon initial insertion of the catheter into tube 320, or upon flow of the fluid from reservoir 330 into the catheter.

Exemplary Defibrillation Treatment Simulation Device

Figure 14:
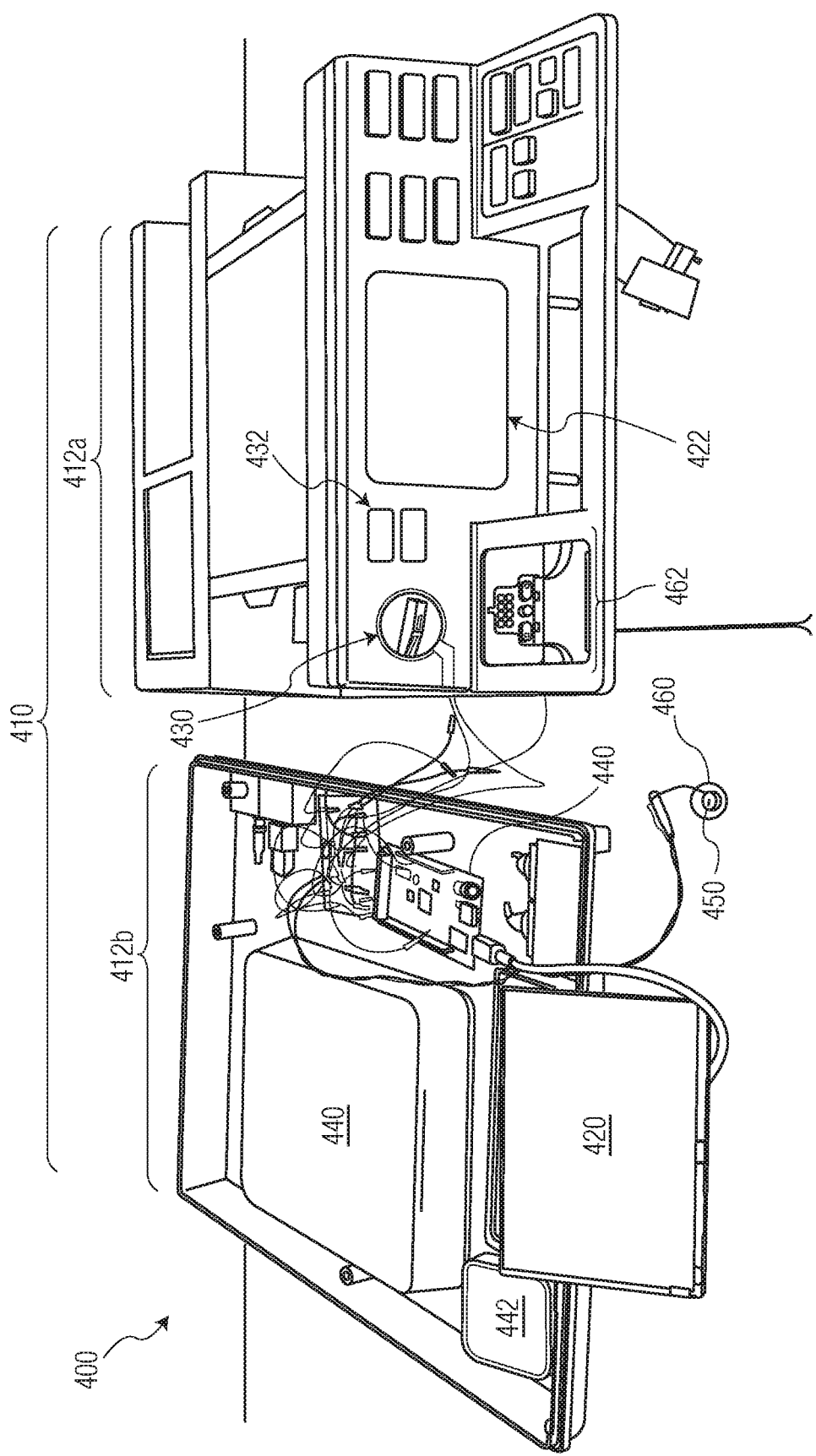
FIG. 14 is a diagram illustrating an exemplary defibrillation treatment simulation device in accordance with aspects of the present invention.

FIG. 14 illustrates an exemplary defibrillation treatment simulation device 400 in accordance with aspects of the present invention. Device 400 is usable to train medical care providers to perform defibrillation treatments. In general, device 400 includes a housing 410, a display 420, one or more input devices 430, and a processor 440. Additional details of device 400 are described below.

Housing 410 houses the components of device 400. In order to provide a realistic simulation, housing 410 has a shape, size, and appearance corresponding to a conventional defibrillator. Housing 410 may be formed from a top portion 412a and a bottom portion 412b. Housing 410 may be configured to be plugged into a standard power outlet in order to power the components of device 400.

In an exemplary embodiment, housing 410 matches the appearance of a CODEMASTER™ 100 defibrillator, provided by Hewlett Packard. Other suitable defibrillators for use in modeling housing 410 will be known to one of ordinary skill in the art from the description herein.

Display 420 is coupled to housing 410. Display 420 displays an image to a user, such as information about a defibrillation treatment or the status of a patient. Display 420 is positioned in a display opening 422 in housing 410. Like housing 410, display 420 has a shape, size, and appearance corresponding to a conventional display for a defibrillator. The selection of display 420 may be based on the type of defibrillator modeled by housing 410. Suitable displays include, for example, liquid crystal displays, light-emitting diode displays, or other visual displays known to those of ordinary skill in the art.

Input devices 430 are provided on housing 410. Input devices 430 enable the user to input signals, instructions, or information into device 400. Input devices 430 may be buttons, knobs, dials, keys, switches, or other structures enabling the input of information. Like display 420, input devices have a shape, size, and appearance corresponding to the input devices on a conventional defibrillator. The selection of input devices 430 may be based on the type of defibrillator modeled by housing 410.

Input devices 430 are operable by the user to simulate applying a defibrillation signal to the subject. Conventional defibrillators include input devices (such as knobs or switches) which, when actuated by the user, cause the defibrillator to apply electrical energy to one or more electrodes attached to a patient. Device 400 includes input devices 430 which, when actuated by the user, cause device 400 to simulate the application of such a defibrillation signal. Such input devices 430 may include a dial for controlling a power of the simulated defibrillation signal, and a button 432 for simulating application of the defibrillation signal. Device 400 does not, however, actually apply a defibrillation signal. Device 400 may simulate the application of a defibrillation signal by providing simulated feedback to the user, or by signaling the subject to provide simulated feedback to the user, as will be discussed in greater detail below.

Processor 440 is provided within housing 410 in communication with display 420 and input devices 430. Processor 440 is programmed to generate a signal to the user that a defibrillation signal has been applied to the subject. In an exemplary embodiment, input devices 430 include a button 432 operable by the user to simulate applying the defibrillation signal to the subject. In this embodiment, processor 440 is programmed to generate a beeping sound (e.g., using one or more speakers) to signal to the user that a defibrillation signal has been applied to the subject.

In an exemplary embodiment, processor 440 is electrically connected to a feedback device 450. Feedback device 450 may be any of the devices discussed above with respect to feedback devices 150 and 250. In a preferred embodiment, feedback device 450 is a tactile signal generator, such as a vibrating motor coupled to the subject in a position where the subject can feel the vibration. In this embodiment, processor 440 is configured to actuate the vibrating motor to provide a tactile signal to the subject in response to the user actuating the input device 430 to simulate the application of a defibrillation signal to the subject. This signal is preferably provided in real time, so that the subject can simulate the role of a patient experiencing a defibrillation signal in response to the user actuating the appropriate input device 430.

In a preferred embodiment, device 400 includes a plurality of patches 460 configured to be connected to the subject. Each patch 460 is coupled to a portion 462 on the outside of housing 410 via a respective wire. Patches 460 are structured to simulate the electrodes that are attached to a patient during defibrillation. To this end, patches 460 may include an adhesive portion for adhering directly to the subject or indirectly, e.g. via one or more layers of clothing or via an overlay. One or more of the patches 460 may include a feedback device 450.

In addition to the above functions, patches 460 may be utilized in certain additional ways. For example, patches 460 may include electrodes for wired coupling with processor 440 in order to detect/display the subject's actual heart rhythm. Such information may be useful for simulating the subject's healthy heart rhythm following the simulated defibrillation. Alternatively, patches 460 may be configured to provide feedback regarding the correct positioning of patches on the subject or on an overlay. For example, in connection with one of the overlays described herein, patches 460 may provide a vibratory or audible signal if they are not positioned in the correct position on the overlay. Such positioning may be detected using known electrical or magnetic sensors for contact with or detection of one or more structures on patch 460.

Processor 440 is further programmed to display a heart rhythm of the subject on display 420. The heart rhythm may be the subject's actual heart rhythm, or may be a simulated heart rhythm. In an exemplary embodiment, device 400 further includes a memory in communication with processor 440. The memory stores one or more simulated patient heart rhythms for displaying by processor 440 on display 420. The stored patient heart rhythms may include unhealthy heart rhythms (such as ventricular tachycardia or ventricular fibrillation) for display prior to simulating application of the defibrillation signal, and may include healthy, normal heart rhythms for display following the simulated application of the defibrillation signal.

Processor 440 may further be configured for wireless communication with one or more computing devices external to housing 410. In an exemplary embodiment, processor 440 includes a wireless transceiver 442 for communication with an external computing device. The display of heart rhythms or the simulated application of a defibrillation signal may be selected, controlled, or triggered wirelessly via the external computing device. Additionally, the actuation of feedback device 450 may be controlled or triggered wirelessly via an external computing device. This set-up may enable an instructor to control the progress and performance of the simulated defibrillation treatment.

Exemplary Thoracic Treatment Simulation Device

Figure 15:
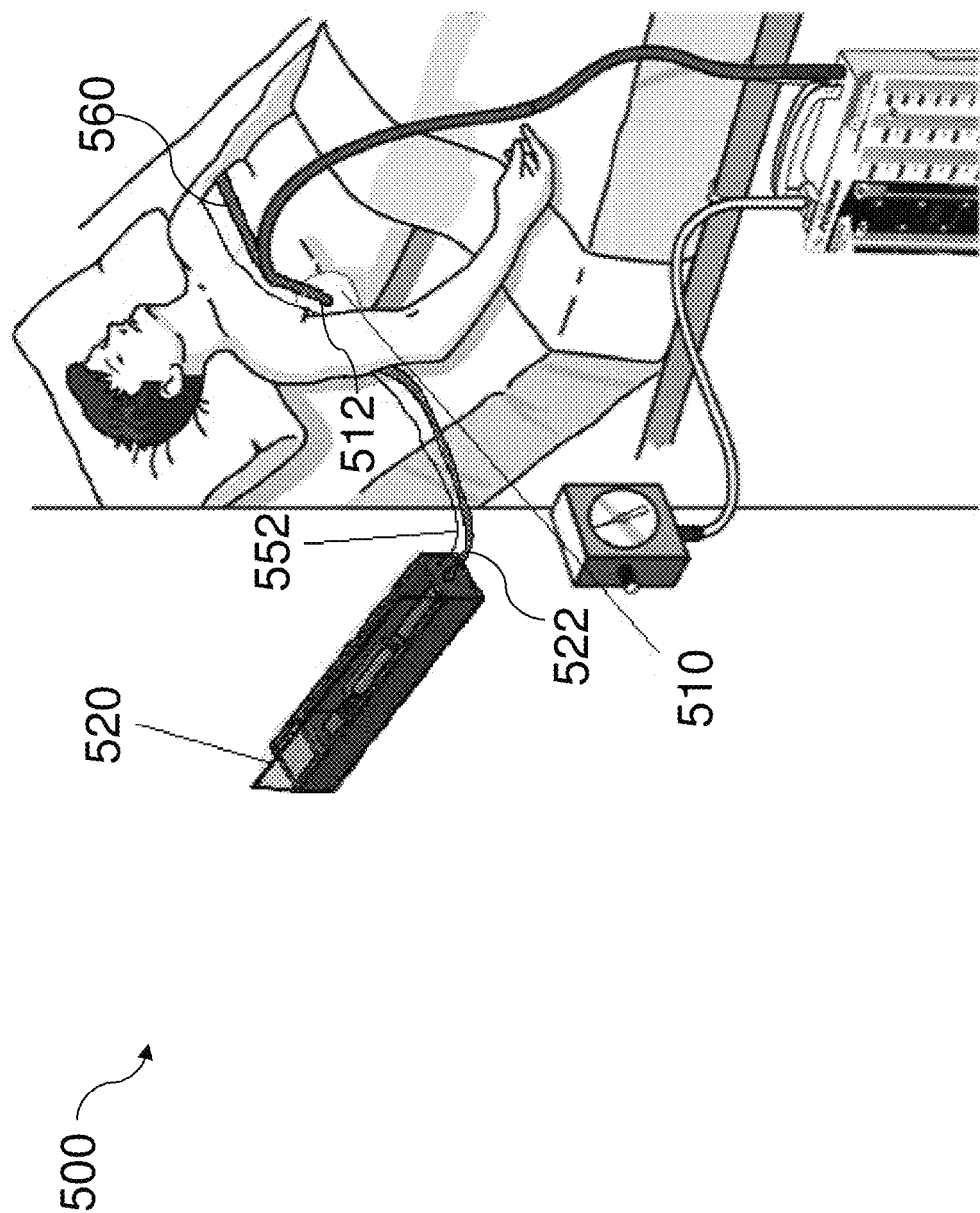
FIG. 15 is a diagram illustrating an exemplary thoracic treatment simulation device in accordance with aspects of the present invention.
Figure 16:
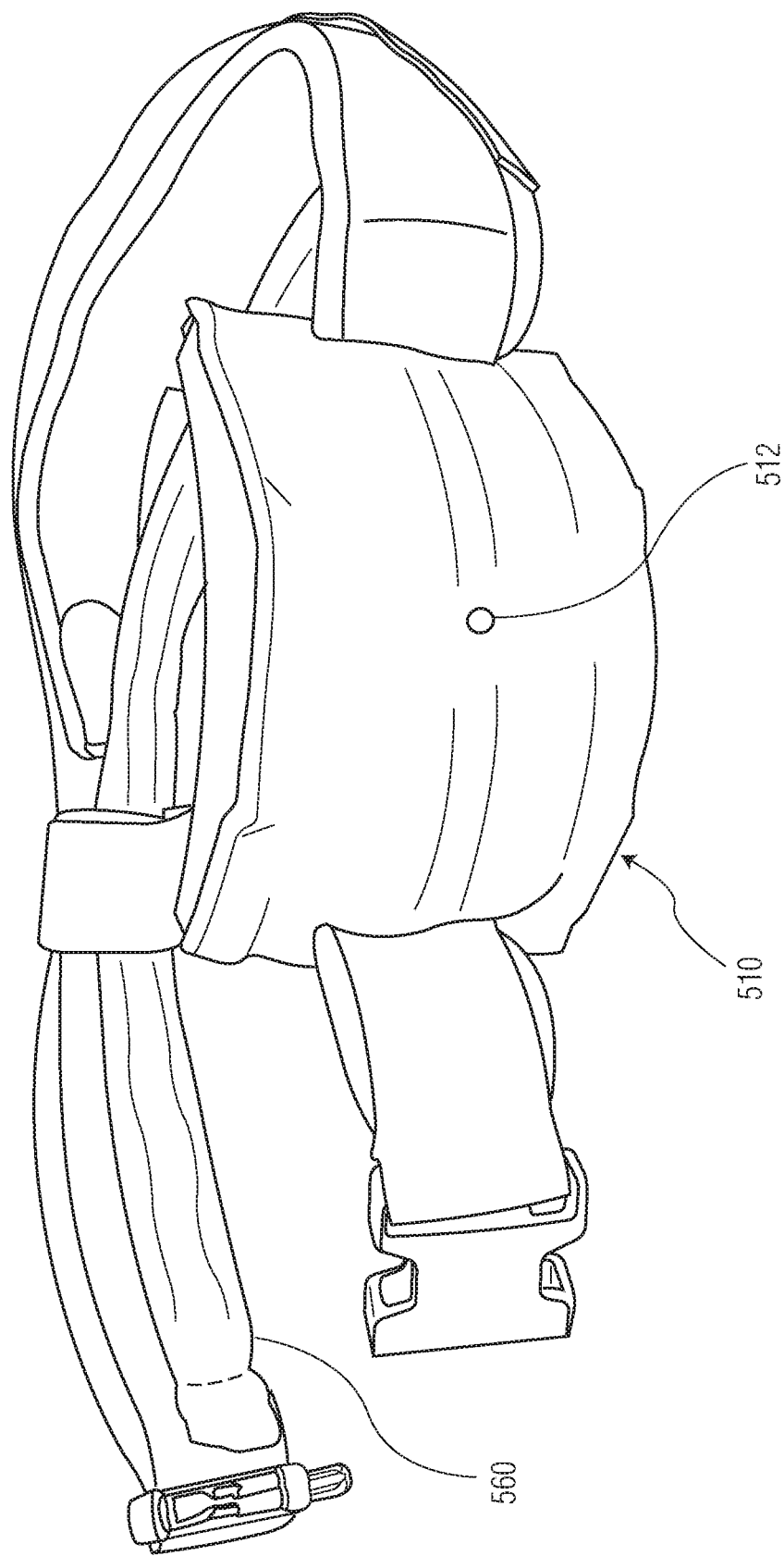
FIG. 16 is an image illustrating an overlay of the thoracic treatment simulation device of FIG. 15.
Figure 17:
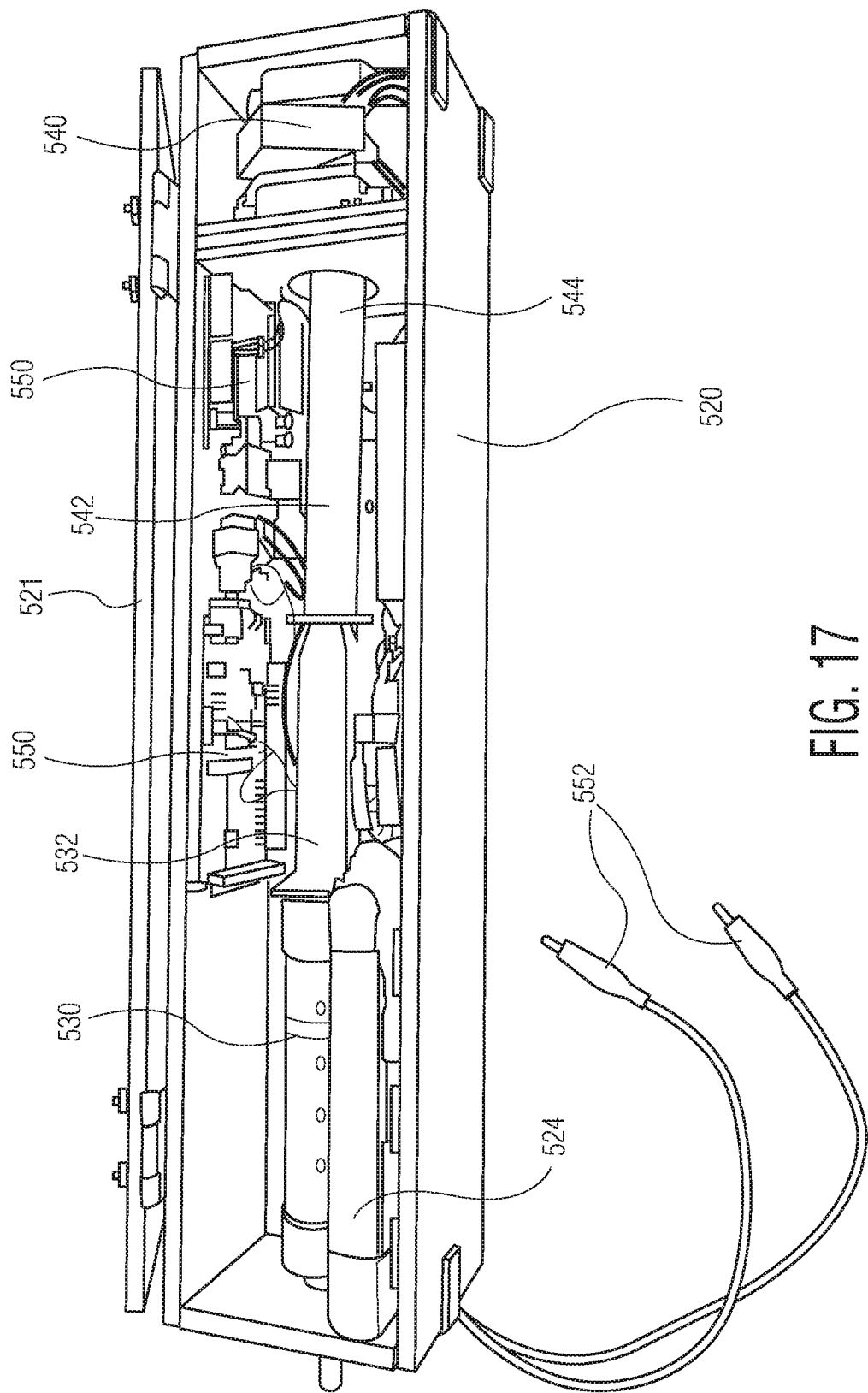
FIG. 17 is an image illustrating a pressure unit of the thoracic treatment simulation device of FIG. 15.

FIGS. 15-17 illustrate an exemplary thoracic treatment simulation device 500 in accordance with aspects of the present invention. Device 500 is usable to train medical care providers to perform thoracic treatments such as chest drainage. In general, device 500 includes an overlay 510, a pressure unit 520, and a processor 550. Additional details of device 500 are described below.

Overlay 510 is configured to be secured to a subject who is playing the role of the patient. In an exemplary embodiment, overlay 510 is adapted to cover at least a portion of the subject's torso, as shown in FIG. 15. Overlay 510 desirably has a thin profile, to allow overlay 510 to closely conform to the shape of the subject's chest. Overlay 510 may include any of the layers described above with respect to overlays 110 and 210 in order to better simulate the appearance and feel of a patient.

In order to better simulate the torso of a patient in need of chest drainage, the surface of overlay 510 is shaped to simulate the contour of the subject's chest, including the subject's ribs. As shown in FIG. 16, overlay 510 includes an opening 512. Opening 512 is sized to be connected with a drainage tube from a conventional chest drainage system, such as those sold by Atrium Medical Corporation of Hudson, N.H.

Pressure unit 520 is in fluid flow communication with opening 512 of overlay 510. Pressure unit 520 may be formed within overlay 510, or may be external to overlay 510. In an exemplary embodiment, pressure unit 520 is provided in a housing 521 external to overlay 510 and connected to opening 512 via a tube 522, as shown in FIG. 15. Tube 522 enters overlay 510 via an area adjacent the subject's armpit, and connects with opening 512 from the interior side of overlay 510. Pressure unit 520 may be provided, for example, underneath a pillow used by the subject, in order to conceal pressure unit 520 from the medical care provider. In general, pressure unit 520 includes a reservoir 530 and a motor 540. Pressure unit 520 may further include one or more power sources 524 for powering motor 540. Additional details of pressure unit 520 are provided below.

Reservoir 530 is coupled for fluid flow with opening 512, e.g. via tube 522. In operation, reservoir 530 stores air that moves into and out of reservoir 530 to simulate respiratory air during simulated breathing of the subject during the simulated thoracic treatment. In an exemplary embodiment, reservoir 530 is part of a syringe pump, as shown in FIG. 17. The syringe pump includes a plunger 532 for applying pressure to the air in reservoir 530 in order to simulate the subject's breathing and cause air to flow into and out of reservoir 530.

Motor 540 is coupled to reservoir 530. Motor 540 is operable to periodically pump air into and out of reservoir 530. In the embodiment in which reservoir 530 is a syringe pump, motor 540 includes a rod 542 and adaptor 544 for coupling motor 540 to the plunger 532 of the syringe pump. Motor 540 pumps air into and out of reservoir 530 by periodically moving the plunger of the syringe pump to change the size of reservoir 530. Motor 540 pumps air into and out of reservoir 530 at a frequency designed to simulate the breathing of the subject, as will be described below. In an exemplary embodiment, motor 540 is a stepper motor. Other suitable motors 540 for use in connection with reservoir 530 will be known to one of ordinary skill in the art from the description herein.

Processor 550 is coupled to motor 540. Processor 550 is configured to operate motor 540 in order to pump the air into and out of reservoir 530 in accordance with a simulated breathing pattern of the subject. In particular, processor 550 may operate motor 540 to pump air into reservoir 530 to simulate the subject inspiring, and to pump air out of reservoir 530 to simulate the subject expiring.

By periodically alternating between these two actions, motor 540 may simulate a breathing rhythm of the subject with air flows into and out of reservoir 530. These breathing patterns may be monitored by a medical care provider performing the simulated thoracic treatment by monitoring air flow into and out of opening 512. Such monitoring may be used to train the medical care provider to detect symptoms in thoracic patients, such as difficulty breathing or thoracic air leak.

The breathing pattern simulated by motor 540 and processor 550 may be the subject's actual breathing pattern, or may be a simulated breathing pattern. In one exemplary embodiment, device 500 includes at least one sensor 560 coupled to overlay 510. Sensor 560 is configured to sense an actual breathing pattern of the subject. Sensor 560 communicates the sensed actual breathing pattern to processor 550. Processor 550 is then configured to operate motor 540 to pump air into and out of reservoir 530 in real time with the sensed actual breathing pattern.

In an exemplary embodiment, sensor 560 comprises a stretchable resistor wrapped around at least a portion of the subject's torso. The resistor acts as a potentiometer. As the resistor expands and contracts in time with the subject's breathing, the resistance of the stretchable resistor changes. The resistor expands as the subject's chest expands during inspiration, and contracts as the subject's chest contracts during expiration. This allows processor 550 to sense the breathing pattern of the subject in time with the changing resistance of sensor 560.

In an alternative exemplary embodiment, device 500 further includes a memory in communication with processor 550. The memory stores one or more simulated breathing patterns for use by processor 550 in operating motor 540. The stored breathing patterns may include unhealthy breathing patterns (such as from patient's suffering from a thoracic air leak), and may include healthy, normal breathing patterns.

Processor 550 may be positioned with overlay 510, or may be external to overlay 510, such as within pressure unit 520. In either embodiment, processor 550 may include one or more wires 552 for connection with motor 540 and/or sensor 560. Processor 550 may further be configured to provide feedback to the subject. For example, an instructor may provide a signal to processor 550, in order to cause processor 550 to actuate one or more feedback devices to prompt the subject to adopt a predetermined breathing pattern, or alter their current breathing pattern in a predetermined fashion. Such feedback could be provided to the subject using any of the structures described herein.

Combined and Other Medical Treatment Simulation Devices

While a number of separate medical treatment simulation devices are described herein, it will be understood to one of ordinary skill in the art that two or more of the exemplary devices described herein may be combined in a single device. For example, the tracheostomy treatment device 100 may be formed as a single device with either the intravenous treatment device 200 and/or the catheter treatment device 300. In these combinations, the overlay may be expanded to include all of the necessary components for simulating the associated medical treatments. Moreover, a full-body overlay be may created by combining the disclosed devices, in order to enable the performance of a plurality of different simulated medical treatments.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A catheter treatment simulation device comprising:
    an overlay configured to be secured to a subject, the overlay comprising an opening sized to receive a catheter;
    a tube coupled with the opening in the overlay;
    a sensor coupled to the tube, the sensor operable to detect an insertion of the catheter into the tube;
    a reservoir adapted to store a fluid, the reservoir coupled to provide the fluid to the tube;
    a valve positioned to control a flow of the fluid between the reservoir and the tube; and
    a processor coupled to the sensor, the processor configured to detect the insertion of the catheter into the tube beyond a predetermined threshold and to open the valve upon the detection of the insertion of the catheter into the tube beyond the predetermined threshold.

2. The catheter treatment simulation device of claim 1, wherein at least a portion of the overlay is shaped to simulate genitalia of the subject.

3. The catheter treatment simulation device of claim 2, wherein the overlay further includes an outer surface adjacent the portion shaped to simulate genitalia, and the reservoir is positioned immediately beneath the outer surface.

4. The catheter treatment simulation device of claim 1, wherein the sensor is configured to detect a force exerted by the catheter.

5. The catheter treatment simulation device of claim 1, further comprising a tactile signal generator, wherein the processor is further configured to actuate the tactile signal generator to provide a signal to the subject upon the detection of the insertion of the catheter into the tube beyond the predetermined threshold.

* * * * *